(12) United States Patent
Slayton et al.

(10) Patent No.: US 6,500,121 B1
(45) Date of Patent: *Dec. 31, 2002

(54) IMAGING, THERAPY, AND TEMPERATURE MONITORING ULTRASONIC SYSTEM

(75) Inventors: Michael H. Slayton, Tempe, AZ (US); Peter G. Barthe, Phoenix, AZ (US)

(73) Assignee: Guided Therapy Systems, Inc., Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,174

(22) Filed: Feb. 10, 2000

Related U.S. Application Data

(63) Continuation-in-part of application No. 08/950,353, filed on Oct. 14, 1997, now Pat. No. 6,050,943.

(51) Int. Cl.[7] .................................................. A61B 8/00
(52) U.S. Cl. .......................................... 600/439; 601/3
(58) Field of Search .............................. 600/439; 601/2, 601/3, 4; 606/1; 604/22

(56) References Cited

U.S. PATENT DOCUMENTS

| | | |
|---|---|---|
| 4,276,491 A | 6/1981 | Daniel ........................ 310/317 |
| 4,757,820 A | 7/1988 | Itoh |
| 4,807,633 A | 2/1989 | Fry |
| 5,209,720 A | 5/1993 | Unger |
| 5,360,268 A | 11/1994 | Hayashi et al. |
| 5,370,121 A | 12/1994 | Reichenberger et al. |
| 5,435,311 A | 7/1995 | Umemura et al. ..... 128/660.03 |
| 5,501,655 A | 3/1996 | Rolt et al. ...................... 601/3 |
| 5,522,869 A | 6/1996 | Burdette et al. .............. 607/97 |
| 5,526,815 A | 6/1996 | Granz et al. ........... 128/660.03 |
| 5,620,479 A | 4/1997 | Diederich .................... 607/97 |

(List continued on next page.)

OTHER PUBLICATIONS

"Noninvasive Estimation of Tissue Temperature Response to Heating Fields Using Diagnostic Ultrasound", Ralf Seip and Emand S. Ebbini, IEEE Transactions on Biomedical Engineering, vol. 42, No. 8, Aug., 1995, pp. 828–839.

"Non–Invasive Detection of Thermal Effects Due to Highly Focused Ultrasonic Fields", Ralf Siep, Emand S. Ebbini, Matthew O'Donnell and Charles A Cain, Department of Electrical Engineering and Computer Science, The University of Michigan.

(List continued on next page.)

*Primary Examiner*—Marvin M. Lateef
*Assistant Examiner*—Runa Shah Qaderi
(74) *Attorney, Agent, or Firm*—Snell & Wilmer

(57) ABSTRACT

An ultrasonic system useful for providing imaging, therapy and temperature monitoring generally comprises an acoustic transducer assembly configured to enable the ultrasound system to perform the imaging, therapy and temperature monitoring functions. The acoustic transducer assembly comprises a single transducer that is operatively connected to an imaging subsystem, a therapy subsystem and a temperature monitoring subsystem. The ultrasound system may also include a display for imaging and temperature monitoring functions. An exemplary single transducer is configured such that when connected to the subsystems, the imaging subsystem can generate an image of a treatment region on the display, the therapy subsystem can generate high power acoustic energy to heat the treatment region, and the temperature monitoring subsystem can map and monitor the temperature of the treatment region and display the temperature on the display, all through the use of the single transducer. Additionally, the acoustic transducer assembly can be configured to provide three-dimensional imaging, temperature monitoring or therapeutic heating through the use of adaptive algorithms and/or rotational or translational movement. Moreover, a plurality of the exemplary single transducers can be provided to facilitate enhanced treatment capabilities.

28 Claims, 15 Drawing Sheets

U.S. PATENT DOCUMENTS

| | | | |
|---|---|---|---|
| 5,655,538 A | 8/1997 | Lorraine et al. | 128/662.03 |
| 5,657,760 A | 8/1997 | Ying et al. | 128/660.03 |
| 5,697,897 A | 12/1997 | Buchholtz | 604/22 |
| 5,722,411 A | 3/1998 | Suzuki et al. | 128/660.03 |
| 5,769,790 A | 6/1998 | Watkins | 600/439 |
| 6,059,727 A * | 5/2000 | Fowlkes et al. | 600/443 |

OTHER PUBLICATIONS

"Transrectal Ablation of Prostate Tissue Using Focused Ultrasound", N.T. Sanghvi, R.S. Foster, R. Bihrle, F.J. Fry, M. Phillips and C. Hennige, 1993 Ultrasonics Symposium, pp. 1207–1210.

"Non–Intrusive Measurement of Microwave and Ultrasound–Induced Hyperthermia by Acoustic Temperature Tomography", S.A. Johnson, Ph.D., D.A. Christiansen, Ph.D., C.C. Johnson, Ph.D., Greenleaf, Ph.D. and B. Rajagopalan, Ph.D., 1977 Ultrasonics Symposium Proceedings, pp. 977–982.

"An Acoustic Phase Shift Technique for the Non–Invasive Measurement of Temperature Changes in Tissues", Brian J. Davis and Padmakar P. Lele, 1985 Ultrasonics Symposium, pp. 921–924.

"Ultrasound Thermometry in Hyperthermia", S. Ueno, M. Hashimoto, H. Fukukita and T. Yano, 1990 Ultrasonic Symposium, pp. 1645–1652.

"Non–Invasive In Vivo Temperature Mapping of Ultrasound Heating Using Magnetic Resonane Techniques", Nadine Barrie Smith, Andrew G. Webb, D. Scott Ellis, Lisa J. Wilmes and William D. O'Brien, Jr., Department of Electrical and Computer Engineering, University of Illinois.

"Limits on Focused Ultrasound for Deep Hyperthermia", H. Wang, R. McGough and C. Cain, Department of Electrical Engineering and Computer Science, The University of Michigan.

"Human Cancer Treatment with Ultrasound", Peter M. Corry, Khaled Jabboury, Elwood P. Armour and Joseph S. Kong, IEEE Transactions on Sonics and Ultrasonics, vol. SU–31, No. 5, Sep., 1984, pp. 444–456.

"Temperature Mapping for High Energy US–Therapy", J. Jenne, A. Werner, J. Debus, P. Huber, K. Jochle, and W.J. Lorenz, German Cancer Research Centre, Heidelberg, Germany, pp. 1–4.

* cited by examiner

IMAGING, THERAPY, AND TEMPERATURE MONITORING ULTRASONIC SYSTEM

CROSS REFERENCE TO RELATED APPLICATIONS

This is a continuation-in-part application of U.S. patent application Ser. No. 08/950,353, filed Oct. 14, 1997, now U.S. Pat. No. 6,050,943.

BACKGROUND OF THE INVENTION

1. Field of the Invention

This invention generally relates to a non-invasive therapeutic ultrasonic system, and more particularly, to a system which is capable of acoustically imaging and heating a certain region to be treated ("the treatment region") in target tissue for therapeutic purposes as well as acoustically monitoring the temperature profile of the treatment region.

2. Description of the Related Art

The absorption of energy in tissue, for example, in the human body produces an increase in temperature, which can be exploited for therapeutic purposes. The irradiation of ultrasound to the target tissue such as in the human body, which has been successfully used for decades mainly in increasingly sophisticated diagnostic imaging applications, also allows the target tissue to absorb a certain amount of energy. Thus, ultrasound may be used in the therapeutic uses.

Specifically, ultrasonic energy at frequencies above 1.5 MHZ has an acoustic wavelength less than 1 mm in the human tissue. This energy is easily controlled in beamwidth and depth of penetration, and has a favorable absorption characteristic in the tissue. These aspects allow the energy to be precisely localized such that regions may be selectively heated while sparing overlying tissue structures.

Ultrasound has significant advantages for therapeutic applications as compared to micro-wave radio-frequency (RF) energy or optical energy (laser light). In contrast with the ultrasound, the RF energy is characterized by long wavelengths in the tissue, with limited to poor control of energy deposition, and high absorption. These aspects of the RF energy constrain its therapeutic usage to large superficial areas. On the other hand, the optical energy which is typically emitted from lasers can be precisely controlled in beamwidth, but the opacity and high absorption in the tissue also limits its use to surface treatment or invasive procedures. Furthermore, the laser and RF energy are emitted from ionizing radiation sources which are typically associated with some risk, unlike acoustic transducers which are typically used for generating ultrasound.

However, in contrast with the diagnostic uses, the therapeutic uses of ultrasound such as hyperthermia and non-invasive surgery have seen relatively little progress due to several technological barriers.

The primary impediment has been a lack of the ability to monitor temperature in the treatment region during the therapeutic treatment process.

Specifically, one of objectives of the therapeutic application is to create a very well-placed thermal gradient in the target tissue to selectively destroy certain regions thereof. For example, hyperthermia technique typically requires to maintain the tissue temperature near about 43 degrees Celsius, while the goal of non-invasive surgery is typically to elevate the tissue temperature above and beyond about 55 degrees Celsius. Moreover, during the therapeutic treatment process, the physiological response of the target tissue is directly related to the spatial extent and temporal duration of the heating pattern. Consequently, in order to appropriately perform feedback and control of the therapeutic treatment process for obtaining successful results, it is absolutely essential to monitor the temperature in the target tissue, for example, so as to know whether or not the temperature in the treatment region has been raised to a level that produces a desired therapeutic effect or destruction in the tissue. In addition, it is preferable to know the temperature distribution in the treatment region and the vicinity thereof for enhancing the therapeutic effect.

In the conventional technique, the therapeutic ultrasonic system has typically relied upon thermocouple probes for monitoring the temperature in the treatment region and the vicinity thereof. However, the thermocouple probes are highly invasive because they have to be inserted into the region-of-interest. In addition, use of the thermocouple probes has necessarily led to very poor spatial resolution since only a small number of probes could be safely embedded in the region-of-interest. Furthermore, the thus embedded thermocouple probes are likely to disturb the acoustic propagation in the tissue and typically cause excessive heating at the probe interface during the therapeutic treatment process. This results in undesirably modified temperature distribution as well as erroneous measurements.

Another factor which has curtailed progress in the therapeutic uses of ultrasound has been the design of the conventional acoustic transducers.

In general, for the therapeutic treatment process, imaging of the treatment region is necessary to determine the location of the treatment region with respect to the acoustic transducers as well as to evaluate progress of the treatment process. Such essential functions of imaging as well as the aforementioned temperature monitoring may be implemented with the same acoustic transducer to be used for the therapeutic purposes, since the acoustic transducers can actually produce an image of the region-of-interest by employing well-established imaging technique such as B-scan imaging. However, the conventional acoustic transducers which are typically employed for the therapeutic purposes are acoustically large, often single-element devices having narrow bandwidth in the frequency domain. Although they are designed to efficiently transmit acoustic energy to the target tissue, the conventional acoustic transducers are typically unsuited for imaging of the treatment region and/or monitoring the temperature profile therein. This precludes development and implementation of these vital functions for performing a desirable precise therapeutic treatment process.

Some prior art references teach the use of ultrasound for therapeutic purposes. For example, U.S. Pat. No. 4,757,820 to Itoh discloses an ultrasound therapy system having functions of imaging and heating the target using ultrasound beams for the therapeutic purposes. The system disclosed therein, however, does not have the temperature monitoring function.

U.S. Pat. No. 5,370,121 to Reichenberger et al. discloses a method and an apparatus for non-invasive measurement of a temperature change in a subject, in particular a living subject, using ultrasound waveforms. The method and apparatus disclosed therein, however, relies on a differential ultrasound image between two successive ultrasound images of the target. In other words, any temperature change is detected as a temperature-induced change in brightness between the two images, which appears in the differential image. Consequently, an actual real-time monitoring of the temperature may be difficult in the disclosed method and apparatus. Moreover, although the method and apparatus can detect changes in the temperature of the target, an absolute value of the target temperature may not be obtained therefrom. In addition, any movement of the target may introduce changes in the differential image, which may cause erroneous results.

Furthermore, although it is not distinctly intended to be applied in the therapeutic treatment process for the target tissue such as in the human body, U.S. Pat. No. 5,360,268 to Hayashi et al. discloses an ultrasonic temperature measuring apparatus in which a temperature of the target medium is calculated using a propagation time of ultrasonic waves which propagated for a predetermined distance in the target medium. The apparatus disclosed therein, however, is mainly described as employing separate ultrasonic elements which respectively function for a transmitter and a receiver of the ultrasonic waves.

While some prior art temperature monitoring techniques exist, see, for example, U.S. Pat. No. 4,807,633 issued to Fry on Feb. 28, 1989, such techniques are complex and have limited applicability. That is, use of such techniques essentially preclude use of the system for purposes of imaging, unless one were to use multiple transducers. In that regard, while two or more physically separated transducers can be used to accomplish imaging and therapy, typically with one configured for imaging and the other for therapy, such a system is susceptible to the generation of imprecise data and is overly complex and expensive.

Thus, it would be advantageous to provide a compact, non-invasive system capable of acoustically performing the therapeutic heating and the imaging of the treatment region in the target tissue as well as the temperature monitoring in the treatment region with a single acoustic transducer. Moreover, it would also be advantageous to provide a compact, non-invasive system capable of performing three-dimensional imaging, temperature monitoring and therapeutic heating of the treatment region to provide a more focused therapeutic treatment process.

In other applications, it would be advantageous to provide therapeutic ultrasonic systems with multiple transducers capable of facilitating the imaging, temperature monitoring, and therapeutic heating functions to obtain imaging and temperature information over a larger area of the region-of-interest and provide therapeutic heating more appropriately to the target tissue, for example, over a larger region-of-interest, with an increased intensity at the treatment region, or more readily focused towards the target tissue.

SUMMARY OF THE INVENTION

In accordance with various aspects of the present invention, a non-invasive therapeutic ultrasonic system is provided, which features a single acoustic transducer and some other subsystems capable of acoustically performing therapeutic heating and imaging of the treatment region as well as acoustically monitoring the temperature profile in the treatment region and the vicinity thereof. Also disclosed herein is a system architecture and associated components as well as algorithms which can be implemented to acoustically achieve the heating, imaging, and temperature monitoring functions. The imaging and monitoring functions allow precise feedback and control of the therapeutic treatment process so that the therapy can be conducted more successfully. In addition, because a single transducer is utilized perfect correspondence is obtained; that is, image artifacts and/or imprecise registration difficulties yielded through use of multiple transducers can be avoided.

A novel acoustic transducer disclosed herein is capable of generating high acoustic power for the therapeutic treatment process, while at the same time providing a good imaging function. Specifically, in order to obtain good lateral resolution in the imaging process, the acoustic transducer of the present invention is preferably divided into an array of sub-elements, each processing acoustic waves with a sufficient bandwidth for good axial resolution in the imaging process.

These imaging requirements are also extended to the acoustic temperature monitoring function of the treatment region. In accordance with various aspects of the present invention, an acoustic temperature measurement subsystem disclosed herein is capable of non-invasively mapping the temperature distribution or profile in the target tissue in real-time. This feature is accomplished by measuring the time-of-flight and amplitude data of acoustic pulses through the region-of-interest while exploiting the temperature dependence of the speed of sound and acoustic attenuation in the target tissue. The acoustic nature of this process allows the same acoustic transducer which is used for the imaging and therapy functions to be used for the real-time temperature monitoring function. Alternatively, the use of the multiple acoustic transducers allows the temperature mapping to be conducted with a higher spatial resolution. The thus gathered valuable information on the temperature in the target tissue can be used to achieve precise control of the spatial distribution of heating, detailed knowledge of the heating duration, and quantitative temperature data during the therapeutic treatment process, which has not been previously possible in the conventional art.

In accordance with other aspects of the present invention, the acoustic transducers disclosed herein can be configured to provide three-dimensional imaging, temperature mapping and therapeutic heating of the treatment region. These three-dimensional features may be realized by any number of methods, such as, for example, the use of adaptive algorithms or the use of mechanical scanning devices.

Additional aspects of the present invention may include the ability to provide therapeutic ultrasonic systems with multiple transducers capable of facilitating the imaging, temperature monitoring, and therapeutic heating functions to obtain imaging and temperature information over a larger area of the region-of-interest and provide therapeutic heating more appropriately to the target tissue, for example, over a larger region-of-interest, with an increased intensity at the treatment region, or more readily focused towards the target tissue.

BRIEF DESCRIPTION OF THE DRAWINGS FIGURES

Preferred exemplary embodiments of the present invention is described in conjunction with the appended drawing figures in which like numerals denote like elements, and:

Figure 10A:
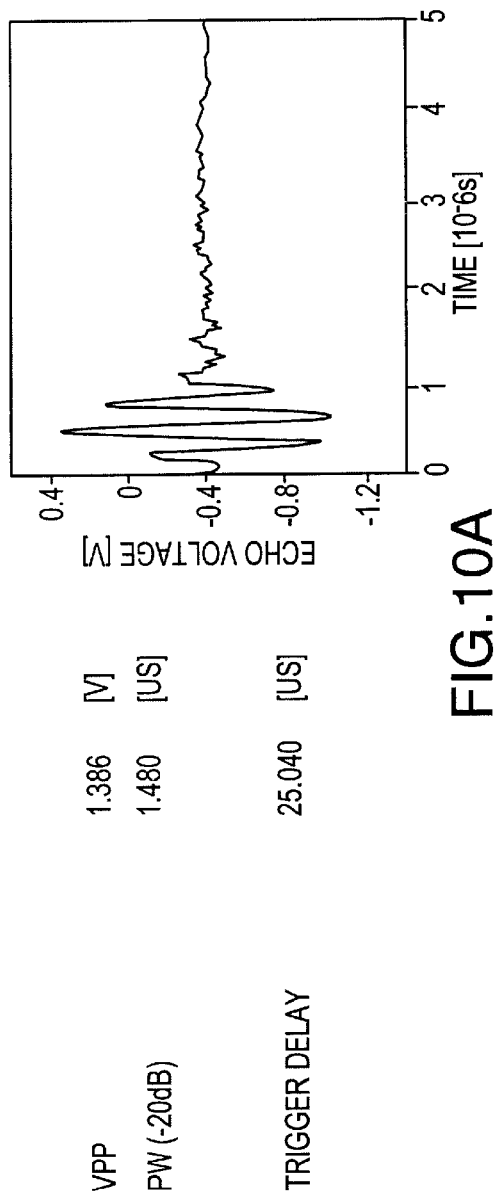
Figure 10B:
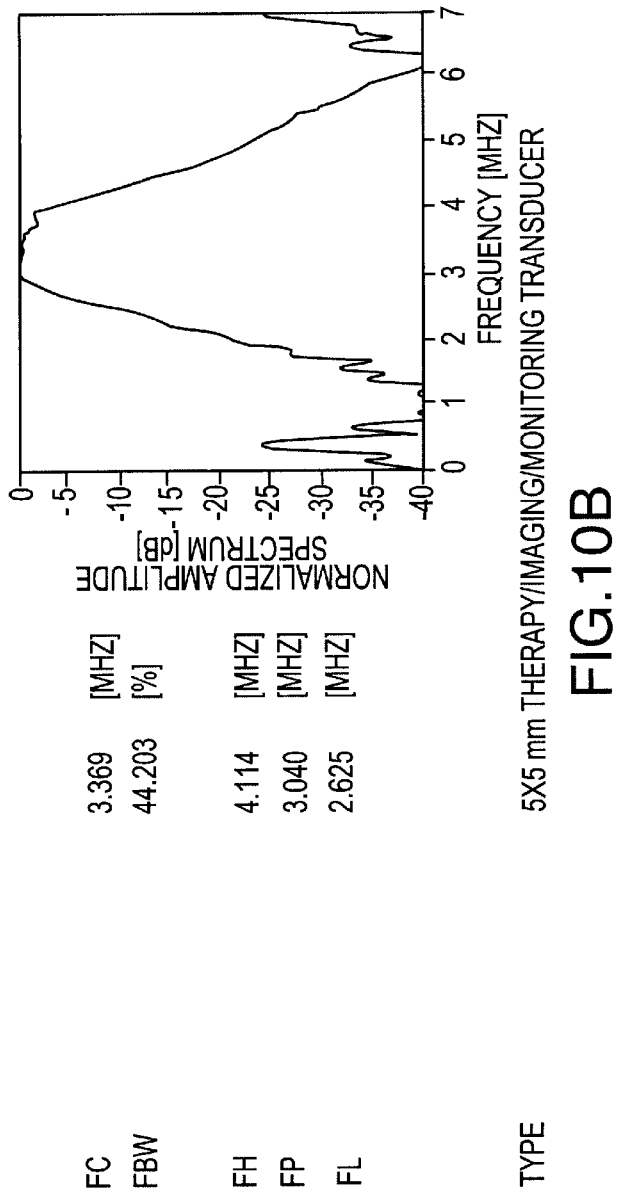
Figure 11:
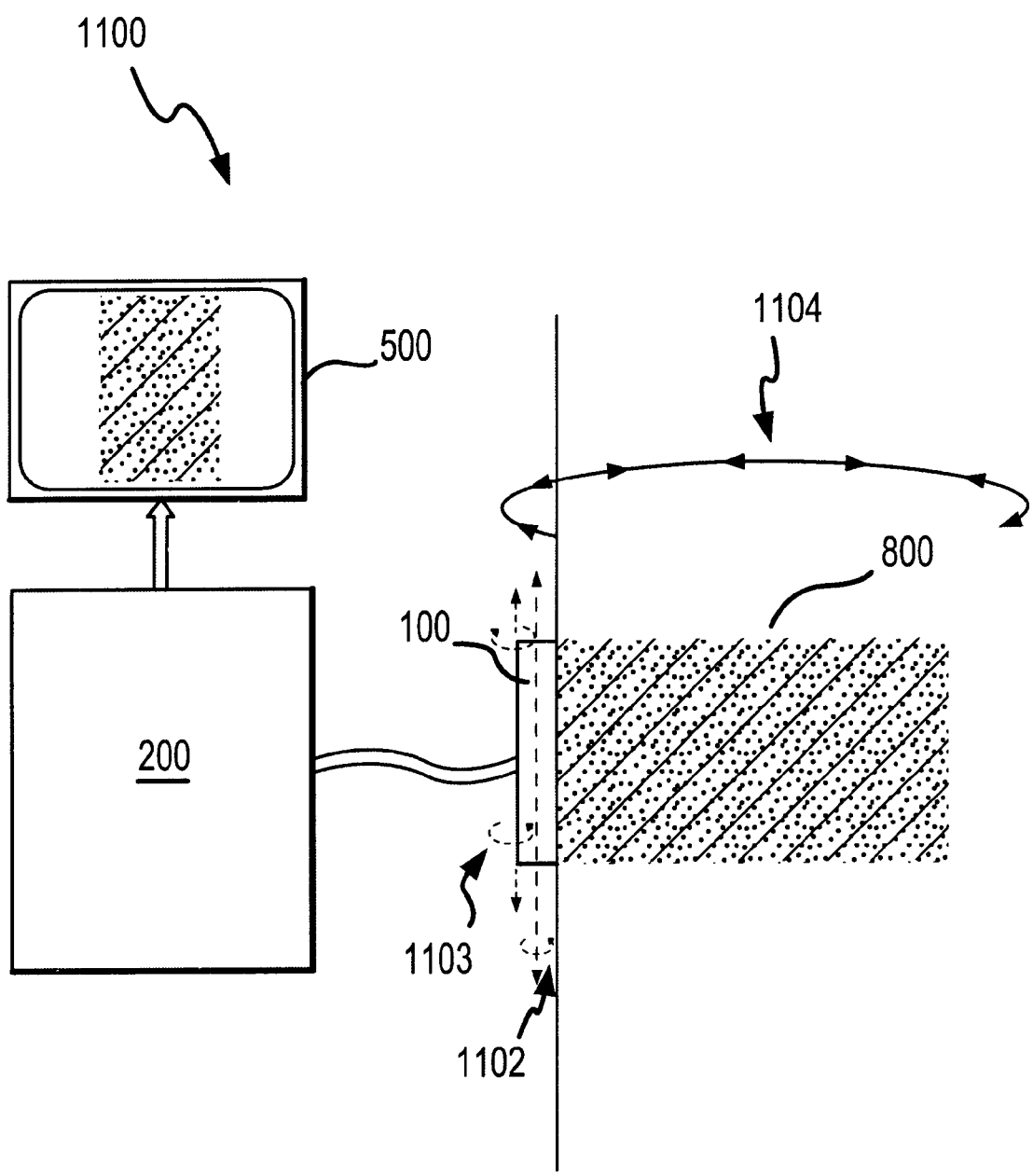
Figure 12:
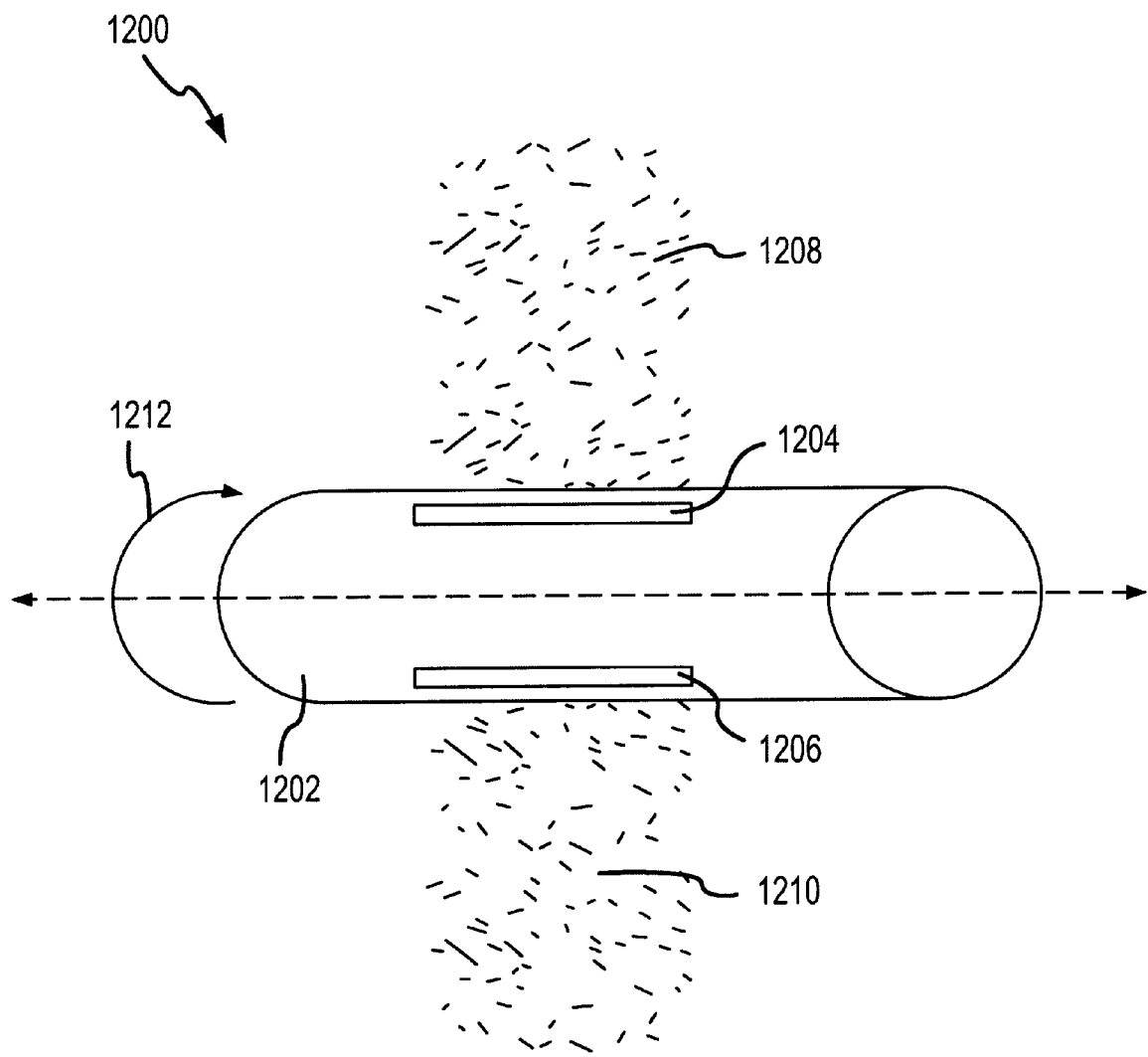
Figure 13:
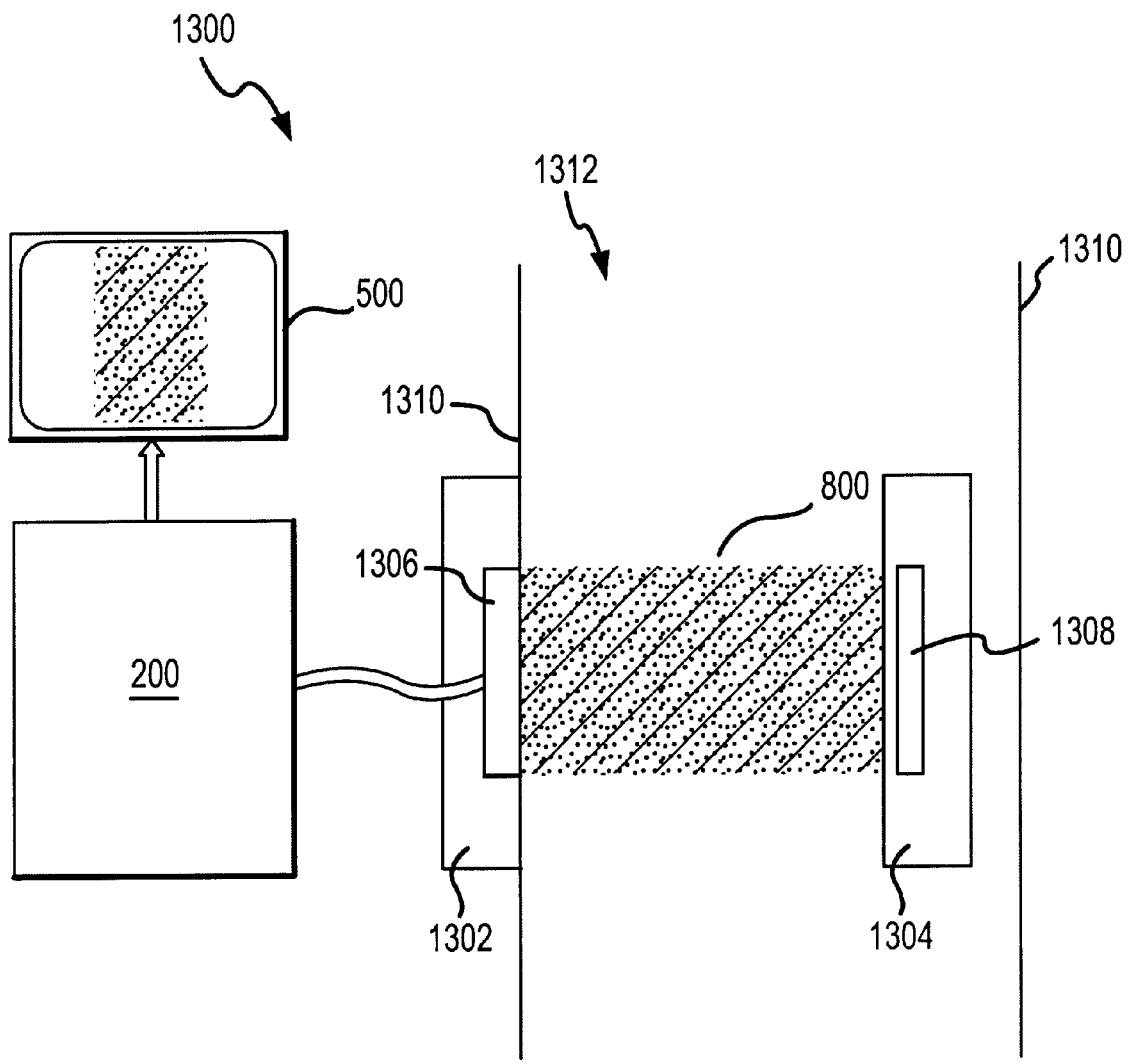
Figure 14:
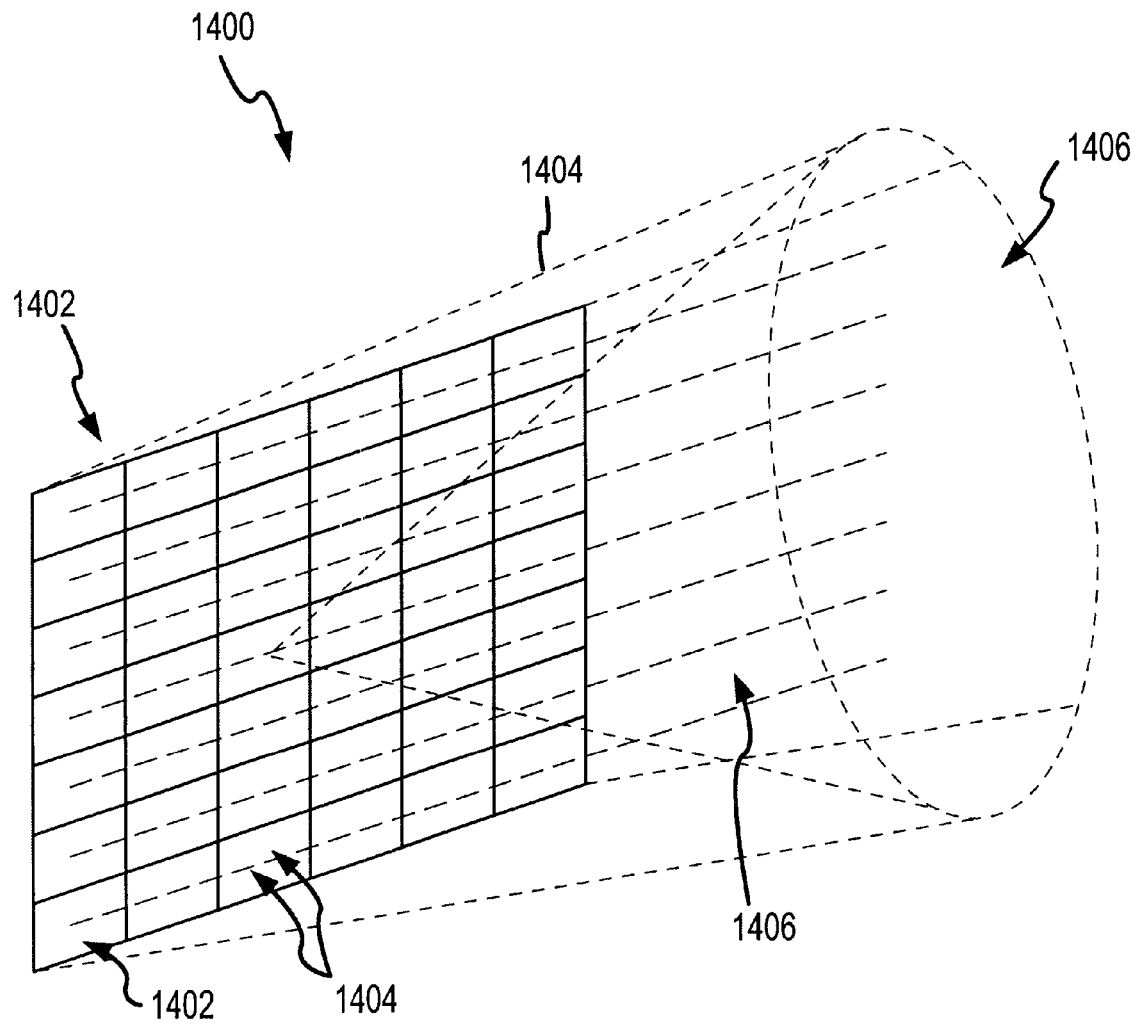

FIGS. 9A–D show the characteristics of an exemplary transducer made in accordance with various aspects of the present invention;

FIGS. 10A–B show, respectively, the pulse echo waveform and the frequency spectrum of the echo of an exemplary transducer made in accordance with various aspects of the present invention;

FIG. 11 is a diagram of an exemplary embodiment of an ultrasonic system having three-dimensional imaging and temperature monitoring capabilities;

FIG. 12 is a diagram of another exemplary embodiment of an ultrasonic system having capabilities for providing imaging and temperature monitoring over a region-of-interest;

FIG. 13 is a diagram of yet another exemplary embodiment of an ultrasonic system multiple transducers; and FIG. 14 is a diagram of an exemplary embodiment of a two dimensional imaging array.

DETAILED DESCRIPTION OF THE PREFERRED EXEMPLARY EMBODIMENTS

A system for achieving successful ultrasonic therapy procedures in accordance with the present invention includes four major subsystems or components. Specifically, they are an acoustic transducer assembly, an imaging subsystem, a therapy subsystem (also referred to as a "therapeutic heating subsystem"), and a temperature monitoring subsystem, which are illustrated in FIGS. 1 through 4, respectively. Although not shown in the drawing figures, the system further includes components typically associated with a therapy system, such as any required power sources, memory requirements, system control electronics, and the like.

Figure 1:
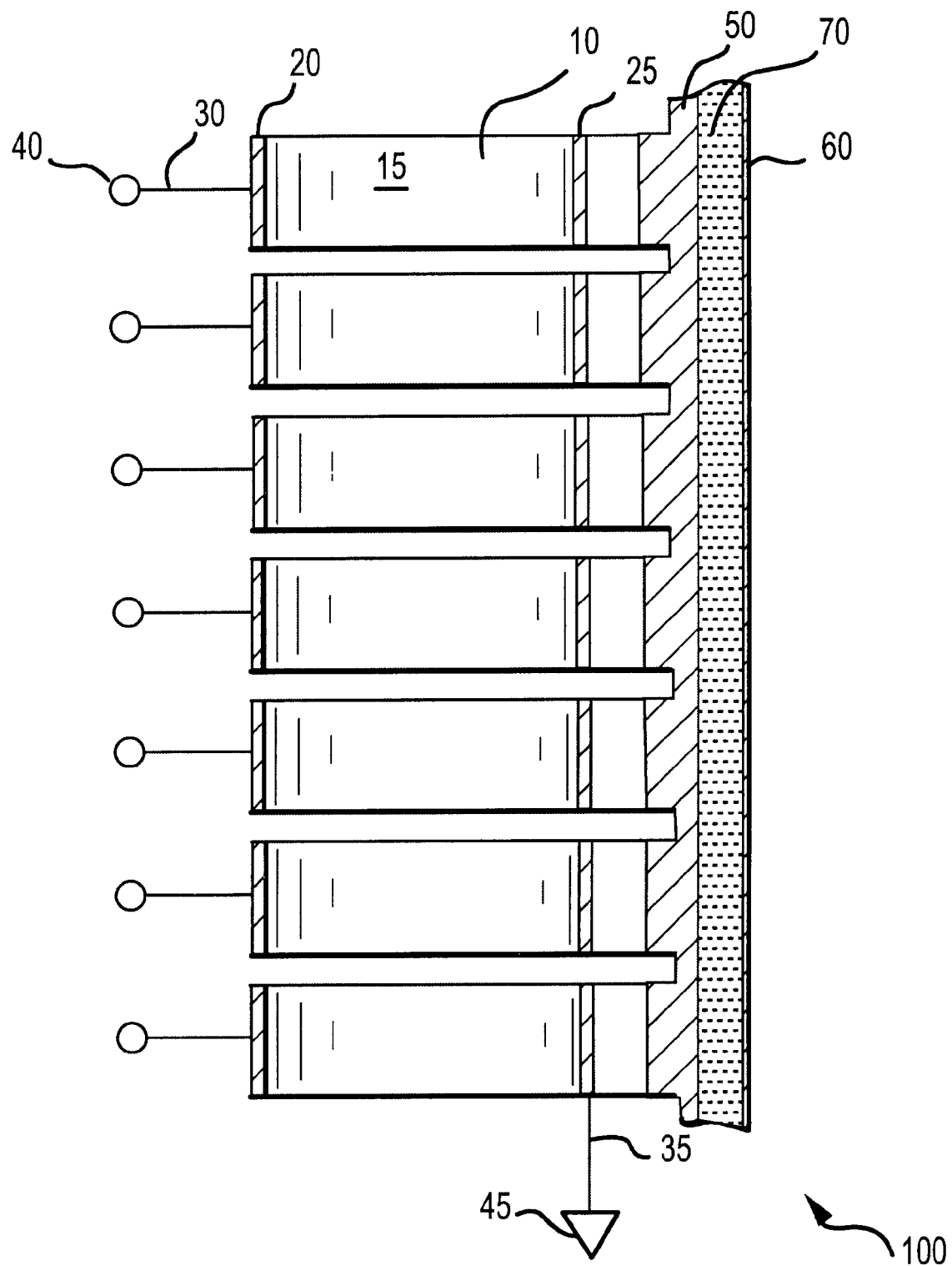
FIG. 1 is a cross-sectional view of an acoustic transducer assembly according to the present invention.

With reference to FIG. 1, the acoustic transducer assembly 100 included in the system of the present invention will be described in detail below. As shown in the cross-sectional view of FIG. 1, the acoustic transducer assembly 100 includes a piezoelectric ceramic plate 10. The air-backed side of the ceramic plate 10 is partially diced to have a plurality of curved (e.g. concave) portions 15 to form a linear array structure. The thickness of the diced ceramic plate is selected to provide a center frequency for example from 500 kHz to 20 MHZ, with lower frequencies yielding deeper penetration and higher frequencies providing greater resolution. The concave portions 15 constituting the transducer array are spaced to achieve good lateral resolution in the imaging function. On the face of each of the concave portions 15, a metal electrode 20 is provided to connect the ceramic plate 10 to the system control electronics (not shown in the figure) via a cable 30 and a terminal 40. The other face of the ceramic plate 10 is configured such as to receive a common metal electrode 25. The common electrode 25 is also connected to the system control electronics via a cable 35 and a terminal 45.

In addition, although a concave portion is described above, it should also be noted that portion 15 may also comprise a substantially flat configuration with a natural focus arrangement, e.g., without a focusing lens. Moreover, portion 15 can also be configured with a substantially flat configuration having a convex or concave lens arrangement. Accordingly, portion 15 may be configured in various manners without departing from the scope of the present invention.

The phrase "air-backed" means that there is no backing material provided on the back side of the acoustic transducer assembly 100, unlike the typical conventional acoustic transducers. Specifically, the conventional acoustic transducers are typically provided with some kinds of the backing layer typically made of a loaded epoxy, such as an alumina powder epoxy. The loaded particles in the backing layer, however, introduces increased acoustic impedance as well as providing scattering surfaces therein. Accordingly, when the generated acoustic waves come to the backing layer and hit the loaded particles included therein, the particles tend to disburse the acoustic waves in different directions into the epoxy matrix so that attenuation increases. As a result, the operational efficiency of the acoustic transducer decreases since some portion of the generated acoustic energy is absorbed in the backing layer. On the other hand, in the acoustic transducer assembly 100 of the present invention, by providing no backing layer on the back end of the ceramic plate 10, the acoustic waves are reflected without being absorbed there to propagate toward the target tissue, resulting in the increased efficiency.

Alternatively, a certain backing layer may be provided as long as it has a very low acoustic absorption so that any significant absorption of the generated acoustic energy does not happen.

On the common electrode 25, one or more acoustic matching layers 50 is bonded using an adhesive such as an epoxy. When a loaded epoxy is used as the adhesive, the acoustic matching layer 50 can be simply cast thereon since they adhere naturally to each other. The acoustic matching layer 50 is intended to obtain appropriate impedance matching between the ceramic plate 10 and the target tissue. Consequently, efficient transfer of acoustic power from the ceramic plate 10 to the target tissue can be maintained to achieve an appropriate temperature increase in the target tissue, resulting in desired therapeutic results. When the acoustic matching layer 50 (or layers) is bonded to the ceramic plate 10 (precisely, to the common electrode 25) with a loaded epoxy, the acoustic impedance can be easily adjusted by changing the amount of metal particles loaded in the epoxy.

At the same time, acoustic matching layer(s) 50 can increase the bandwidth of the emitted acoustic waves in the frequency domain. This aspect is suitable for the effective imaging function.

Specifically, in order to improve the sensitivity in the imaging function, it is preferable that the emitted acoustic waves are very pulsive in the time domain since acoustic pulses with a very short pulse width can produce clearly distinct echoes from different interfaces existing in the target tissue. The shorter the width of the acoustic pulses is, the more clearly the distinct echoes can be resolved, resulting in improved resolution in the obtained images. The short pulse in the time domain means a wide range in the frequency domain which covers a large spectrum. On the other hand, however, when considering an efficient transmission of the acoustic energy from the acoustic transducer assembly 100 to the target tissue which is important for the therapeutic treatment process, it is preferable to use stable acoustic waves such as "continuous waves" or gated bursts, which in turn means that the bandwidth thereof in the frequency domain is narrow. Thus, trade-off between the efficiency in the therapeutic function and the sensitivity in the imaging function has to be satisfied by appropriately setting the bandwidth of the acoustic waves to be emitted.

Without acoustic matching layer(s) 50, the bandwidth of the emitted acoustic waves is determined mainly based on the design of the ceramic plate 10 which actually generates the acoustic waves. This results in the limited degrees of freedom for adjusting the bandwidth. Providing one or more acoustic matching layer(s) 50 makes it possible to properly adjust the bandwidth in a wide range without substantially changing the design of the ceramic plate 10.

Typically, the thickness of the acoustic matching layer 50 is set to be on the order of a quarter of a wavelength of the acoustic waves. In addition, it is preferable that the acoustic impedance of the acoustic matching layer 50 be set to be approximately equal to the square root of the acoustic impedance of the ceramic plate 10 times the acoustic impedance of the target tissue or, more preferably, the acoustic impedance of the ceramic plate raised to the ⅓ power, times the acoustic impedance of the target tissue raised to the ⅔ power. Also, multiple matching layers may be used, of course, with suitable changes in layer impedances.

The acoustic matching layer 50 can be made of various types of materials, such as ceramics, plastics, metals and a composite material thereof. Preferably the matching layer may exhibit good thermal conductivity and low acoustic attenuation. Matching layer (or layers) 50 may be cut or diced, such as shown on FIG. 1, to maintain high acoustic isolation, i.e., low acoustic crosstalk. However, any heating of the matching layer(s) of ceramic may be controlled via the duty cycle of the drive signal or via active or passive cooling methodologies. In addition, any other conventional cooling technique and/or methodology may be utilized.

Although not shown on FIG. 1, it should be appreciated that transducer assembly 100 may be provided with a back layer (not shown) suitably configured to modify the bandwidth of the transducer and/or serve as a heat sink.

The ceramic plate 10 and other related components configured as set forth above are coupled to the target tissue via a fluid 70 circulating between the acoustic matching layer 50 and an acoustically-transparent membrane 60. The fluid 70 also functions as a coolant for the ceramic plate 10 and the acoustic matching layer 50 and may also aid in controlling the temperature of the tissue at the interface. Temperature control via a circulating fluid, thermoelectric cooling module and/or pneumatic or other devices may also be utilized in accordance with various aspects of the present invention. Furthermore, the acoustic transducer assembly 100 having the aforementioned configuration is enclosed in a water-tight housing (not shown in the figure).

The circulating fluid 70 has two major functions as mentioned above. One of them is to couple the ceramic plate 10 and the acoustic matching layer 50 to the target tissue. The other is to remove the waste heat away from the acoustic transducer assembly 100. In particular, the energy conversion efficiency of the acoustic transducer assembly 100 is typically about 80%, and consequently, some portion of the input electrical power becomes the waste heat. When a large amount of electrical power is input to the acoustic transducer assembly 100, the assembly 100 is heated up. This may result in reduced efficiency and altered operational characteristics, which are likely to produce adverse effects on the therapeutic purposes. The circulating fluid 70 therefore keeps the acoustic transducer assembly 100 at a stable and constant temperature by cooling it off.

The fluid 70 is typically water. Alternatively, any suitable mineral oil, plant oil, or other suitable liquid could be used as the fluid 70.

Figure 2:
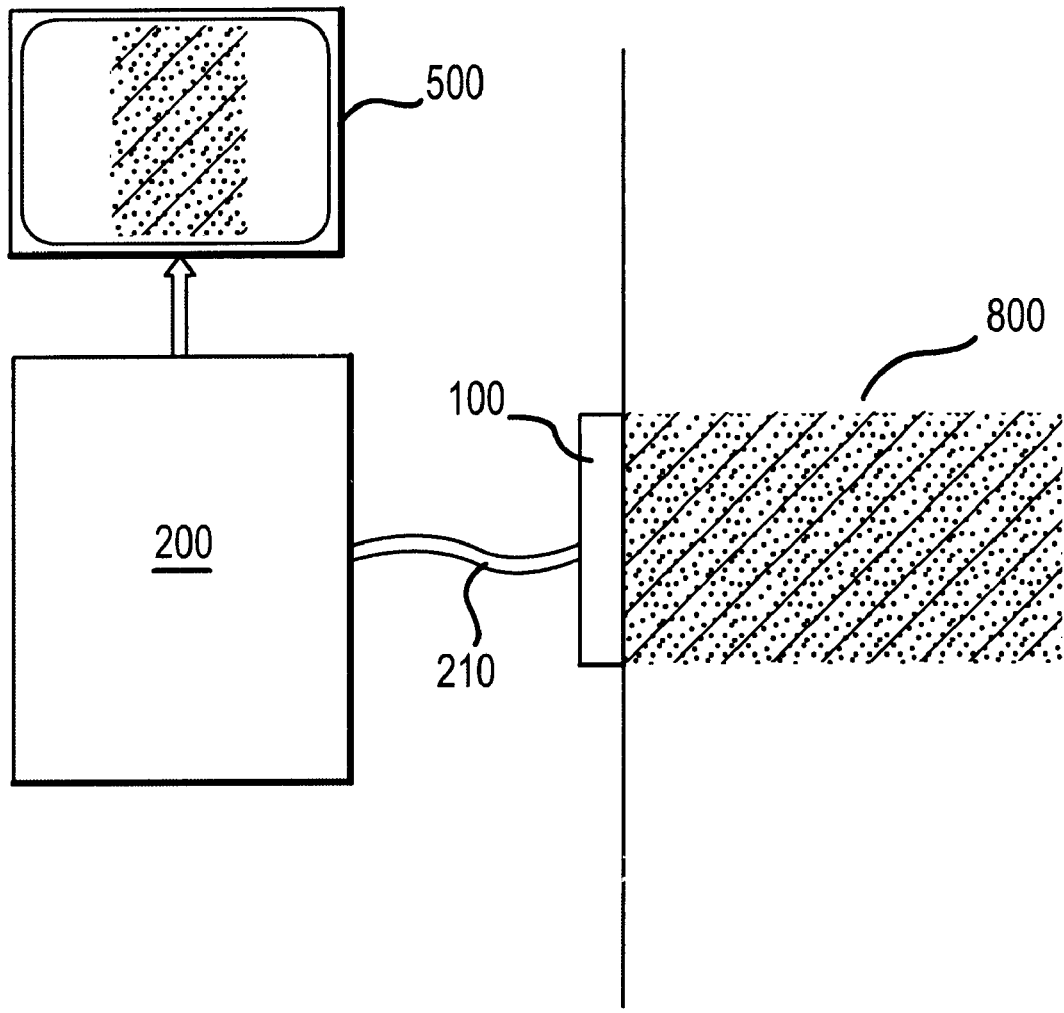
FIG. 2 is a diagram of an imaging subsystem interfaced to the acoustic transducer assembly according to the present invention.

With reference to FIG. 2, an imaging subsystem 200 which is interfaced to the acoustic transducer assembly 100 is described below. The imaging subsystem 200 connected to the acoustic transducer assembly 100 via a cable 210 includes a beam forming control unit. The unit is operated so that the acoustic transducer assembly 100 scans the region-of-interest, including the treatment region, in the target tissue 800 with the acoustic waves. The returning acoustic signal is received by the acoustic transducer assembly 100, and then sent to the imaging subsystem 200 to generate ultrasonic images of the treatment region. The thus generated image is displayed on a video display terminal 500 to assist the user in appropriately positioning the acoustic transducer assembly 100 with respect to the treatment region in the target tissue 800 prior to actually commencing the therapeutic treatment process.

Figure 3:
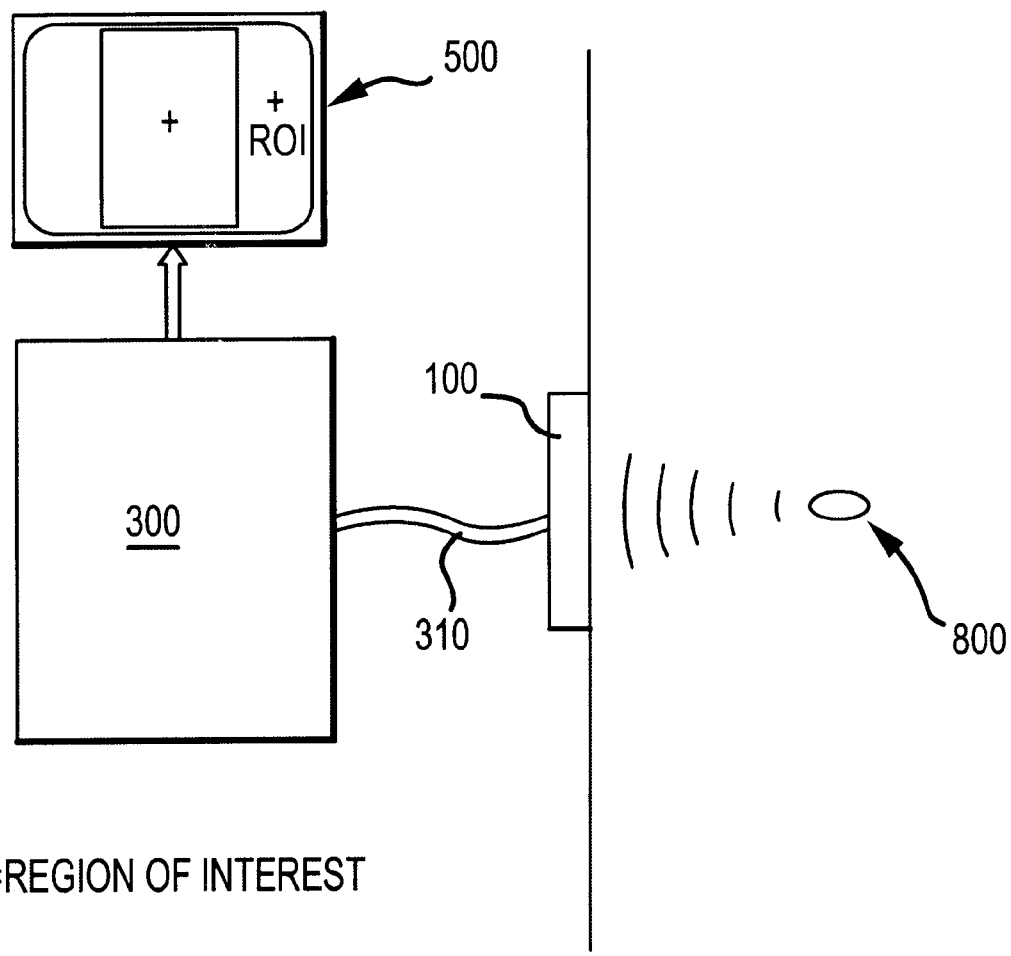
FIG. 3 is a diagram of a therapy subsystem interfaced to the acoustic transducer assembly according to the present invention.

With reference to FIG. 3, a therapy subsystem (a therapeutic heating system) 300 which is interfaced to the acoustic transducer assembly 100 is described below.

The therapy subsystem 300 connected to the acoustic transducer assembly 100 via a cable 310 includes power RF drivers which are interfaced to the linear array of the acoustic transducer assembly 100, i.e., to each of the respective portions 15 of the ceramic plate 10 shown in FIG. 1. The power RF drivers are also connected to the common electrode 25 provided on the other face of the ceramic plate 10. By appropriately applying RF signal voltages to the ceramic plate 10 from the thus connected power RF drivers, high power acoustic energy is generated. The drivers are controlled in-time so that the acoustic transducer assembly 100 transmits, steers, and/or focuses the acoustic waves to the region-of-interest including the treatment region in the target tissue 800. Heating power and heating time as well as transducer anodization are all controlled during the therapeutic treatment process to achieve the proper heating pattern and therapeutic dosage. The control can be supplemented by the feedback of information from the temperature monitoring subsystem described later.

In connection with yet another embodiment of the present invention, temperatures are monitored in a manner calculated to avoid tissue motion artifacts. For example, in the case where a localized region is heated, in accordance with this embodiment of the present invention, the heated region is interrogated with a pulse echo signal substantially immediately thereafter. In such a case the echo from the heated region will be changed in time and amplitude. For example, the acoustic attenuation in tissue approximately doubles from 50° C. to 70° C. Preferably, the region is measured immediately before and after heating and thus, tissue motion artifacts are avoided, as well as any acoustic propagation effects.

In the case where only a small region is treated at a time, an isothermal region about the hot spot is engendered. Therefore, the time-of-flight and the amplitude of wave incident on the heated region is the same before and after the therapeutic energy is delivered. Thus, the amplitude change and time change measured after therapy will be due substantially to the tissue treated.

Figure 4:
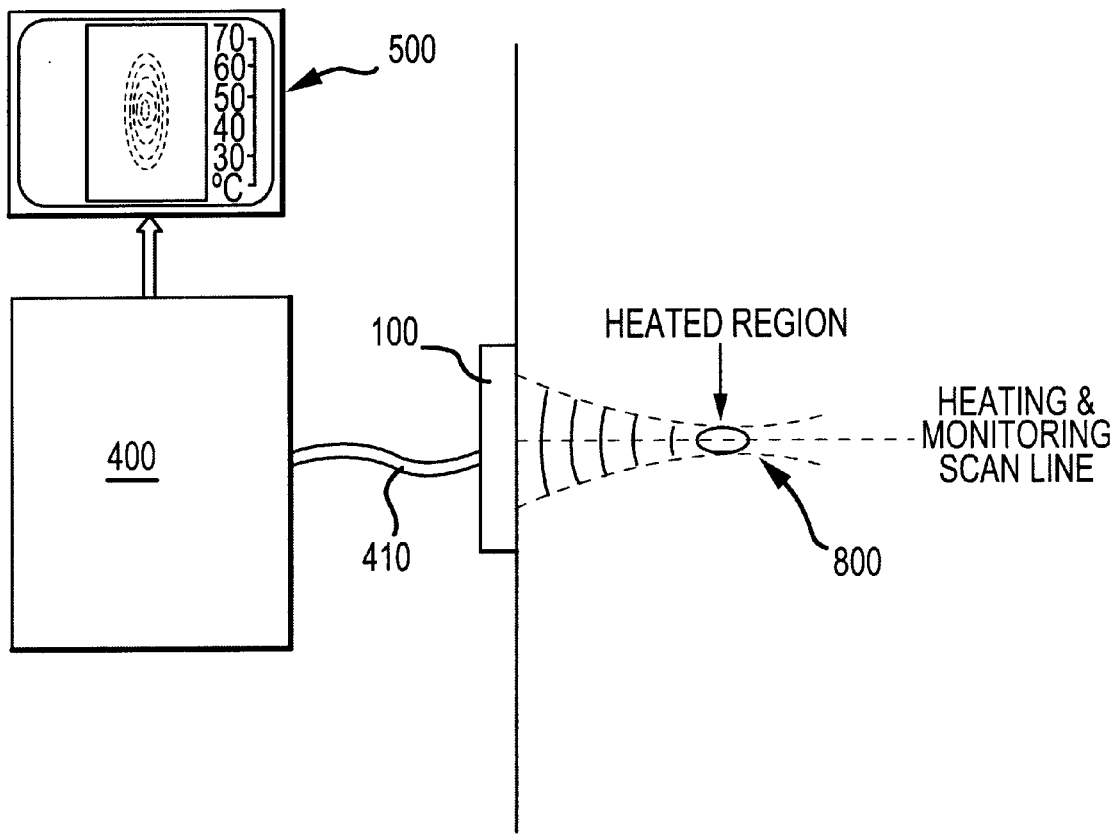
FIG. 4 is a diagram illustrating a temperature monitoring subsystem according to the present invention.

With reference to FIG. 4, a general schematic utilizing this approach is shown where transducer assembly 100 is used to heat a small region 800. As shown, the temperature monitoring subsystem 400 is connected to display 500. Temperature monitoring subsystem 400 is also connected to transducer assembly 100, such as by a suitable cable 410. In accordance with this aspect of the present invention, the whole volume is scanned, and by sweeping the pulse echo the effective thermal dose (time/temperature history) (e.g. recrossed volume) can be determined. In the context of the present invention the term thermal dose relates to the temperature and time of duration integral function by which, for example, a determination of necrosity can be made.

Figure 5:
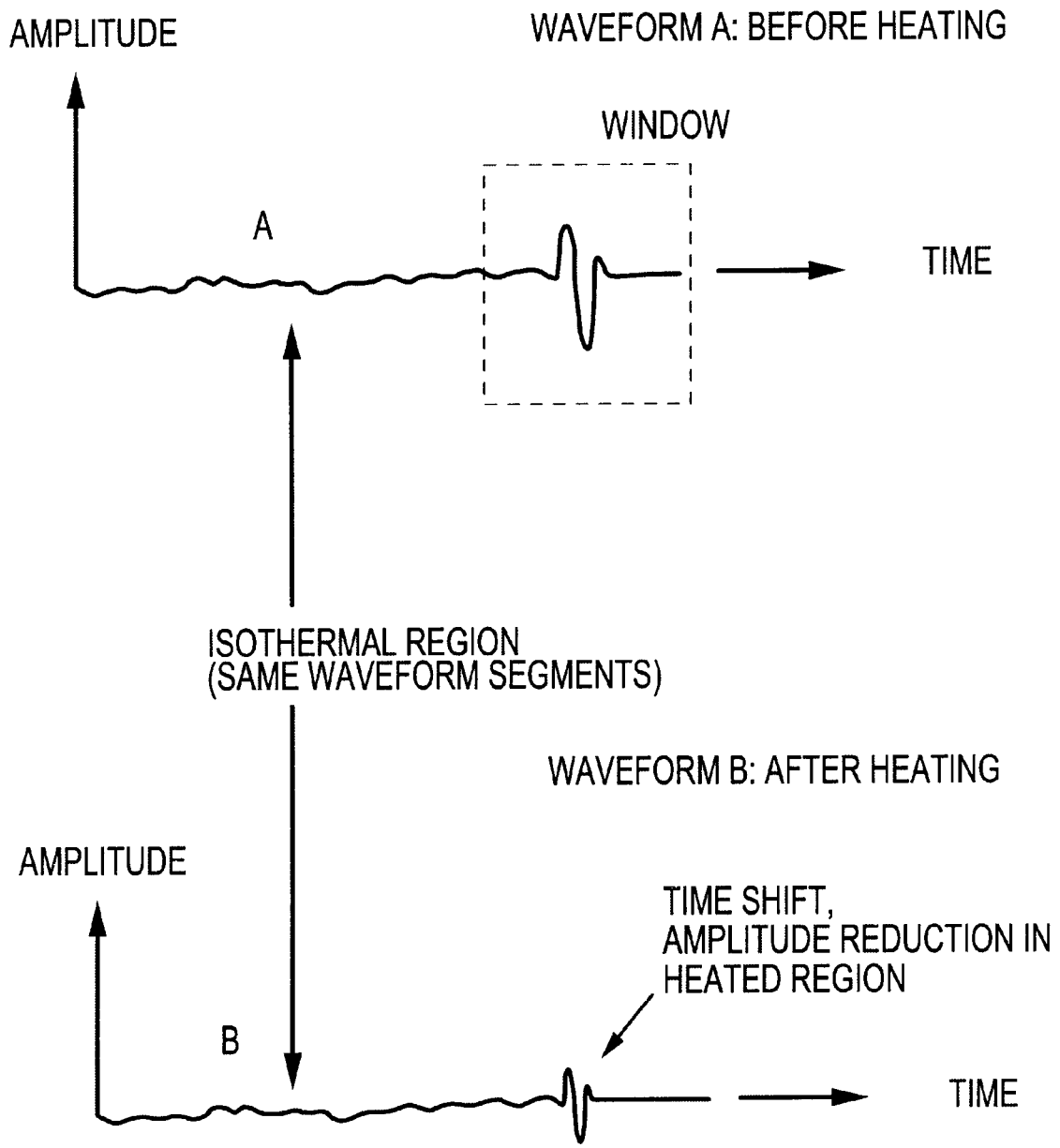
FIG. 5 depicts waveforms of heated and unheated states illustrating the time shift and amplitude change of the echo in the region of interest.

With reference to FIG. 5, the echo waveform in a windowed region of a waveform A obtained before heating and a waveform B after heating can be examined, and based on the time-duration and spatial extent of the heated area, i.e. the time shift of the echo in the heated region and tissue and thermal properties, the temperature can be determined.

Alternatively, instead of evaluating the time shift, the echo amplitude in the windowed region could be examined. In accordance with this aspect of this embodiment of the present invention, when the amplitude of the signal in the windowed region begins to rapidly fall, the temperature will be in the 50° C. to 70° C. range. In this manner the effective necrosed volume can be determined.

It should be appreciated that in accordance with various aspects of the present invention, both echo time shifts and amplitude changes may be employed. For example, by scanning the windowed region in one, two, or three dimensions, a temperature map or image can be obtained.

Of course this technique may also be performed on an incremental basis to compensate for changes in temperature along some line, including, for example, before/after the hot spot. For example, by windowing out regions from the transducer to the region of interest and in each region computing the temperature from attenuation techniques or phase shifts, a temperature profile can be accurately determined.

Figure 6:
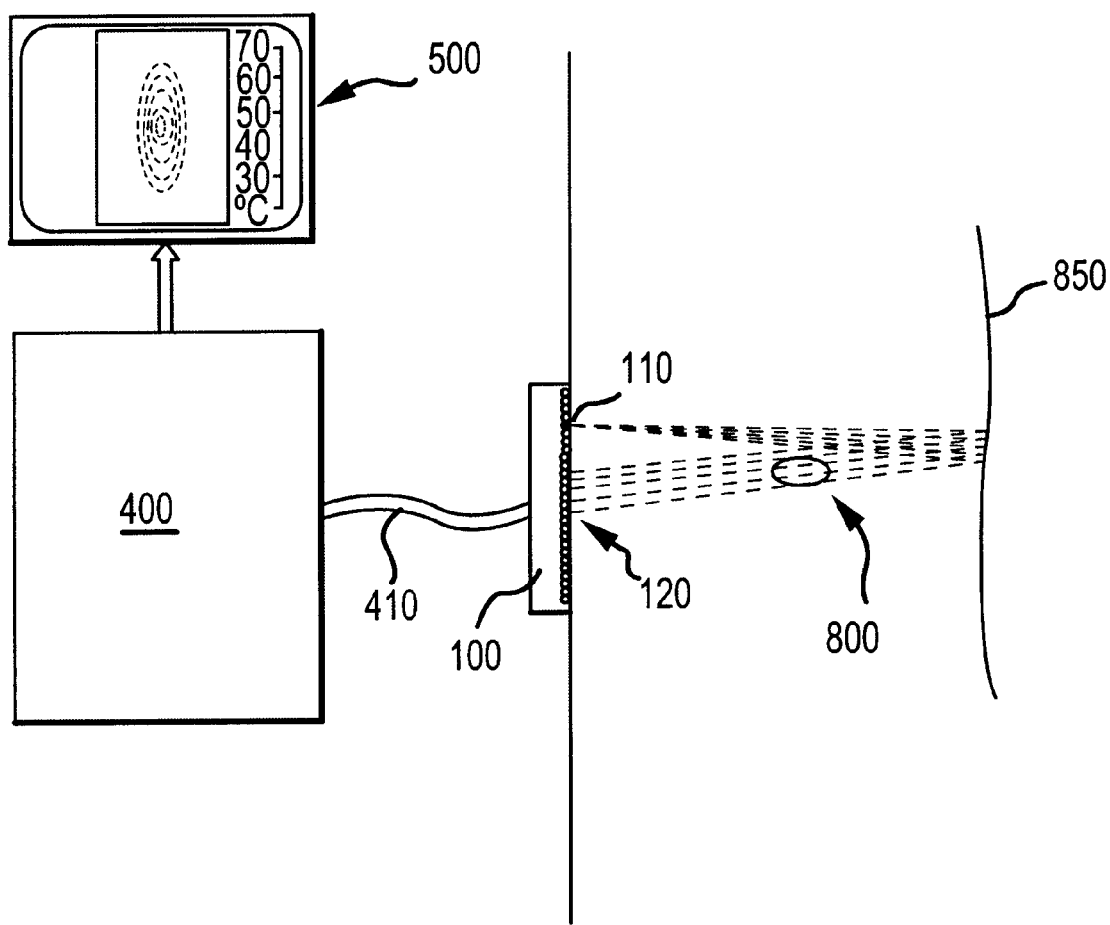
FIG. 6 is a diagram of a further embodiment of a temperature monitoring subsystem interfaced to the acoustic transducer assembly according to the present invention.

With reference to FIG. 6, a temperature monitoring subsystem 400 which is interfaced to the acoustic transducer assembly 100 and monitor 500 is described below. The temperature monitoring subsystem 400 connected to the acoustic transducer assembly 100 via a cable 410 includes a control unit. The unit is operated so that the temperature mapping process as follows is properly conducted.

In particular, an acoustic pulse wave is first generated by a single transmitting element 110 among the linear array of the acoustic transducer assembly 100. The thus generated acoustic pulse wave propagates into the target tissue 800 and through any temperature gradients. Since the speed of sound in the target tissue 800 exhibits temperature dependency, the acoustic wavefronts will be sped up or slowed down in certain regions based on the temperature gradients existing in the target tissue 800. Upon reaching a boundary 850 used for reference, the acoustic wavefronts are reflected thereon so that the reflected wavefronts, i.e., the echoes come back towards the acoustic transducer assembly 100, where they are detected by remaining elements 120 in the linear array. Upon the echoes returned from the target tissue 800 are detected by the acoustic transducer assembly 100, a certain signal is sent to the temperature monitoring subsystem 400 in which the time-of-flight data of the detected echoes (i.e., the returned acoustic wavefronts) which is a period of time required from the emission of a certain acoustic pulse to the detection of the corresponding echo (the reflected acoustic wave) is calculated. The above transmitting-and-detecting sequence is repeated for each unique transmitter-receiver combination to form a large data set.

Finally, using propagation path data, the obtained time-of-flight data is numerically converted into speed data of sound in the target tissue, and then further into a matrix of temperature values. Specifically, the speed V of sound (in this case, the speed of the ultrasonic wave) in the target tissue is expressed as follows:

$$V = V_0 + f(T) \quad (1)$$

where $V_0$ represents the speed of sound at a certain temperature in the target tissue, T is a temperature of the target tissue, and f(T) is a function of T. Furthermore, the speed V of sound is also expressed as follows:

$$V = L/t \quad (2)$$

where L represents the length of the propagation path while t represents the propagation time (i.e., the time of flight) which is required for the sound (i.e., the acoustic wave) to cover the propagation path of the length L.

As a result, from the above-mentioned expressions (1) and (2), the temperature T of the target tissue can be calculated based on the measured time-of-flight (the propagation time) data t with using values for L, $V_0$ and f(T). Typical values for $V_0$ and f(T) are known in the art or readily measured in experiments. On the other hand, the propagation path length L for the above calculation can be determined in several manners.

For example, a small biopsy needle, typically metallic, with a square cross-section can be placed in the target tissue until reaching a predetermined depth. Such a metallic needle provides a large amount of reflection of the acoustic waves, thereby functioning an artificial reference boundary placed at the predetermined known depth in the target tissue.

Alternatively, instead of providing the artificial boundary, any natural boundaries existing in the target tissue can be used as the reference boundary which provides the basis of calculating the propagation path length. Such natural boundary will include a tissue-to-air boundary, a tissue-to-water boundary, a tissue-to-bone boundary, and the like.

When any actual artificial or natural boundaries are not available in the target tissue as the reference boundary, an imaginary boundary or a virtual boundary can be produced. When one acoustic pulse or wave is emitted toward the target tissue at a time of zero (0) and the corresponding returning echo is detected at a time of X, then the specific pulse or wave has traveled in the target tissue over a distance which is approximately calculated as X times the speed of sound. Thus, the signal processing and analysis in the subsequent processes can be conducted based on this particular echo as the reference.

Analogous to the time-of-flight data, and use thereof as described herein, in accordance with various aspects of the present invention, the amplitude of the returned echoes can also be used to create an image of the acoustic attenuation.

The obtained temperature data is sent to the video display terminal 500 for visualization by the user, and also sent to the therapy subsystem 300 previously described for dynamic control of the heating process for the therapeutic treatment purposes.

Figure 7:
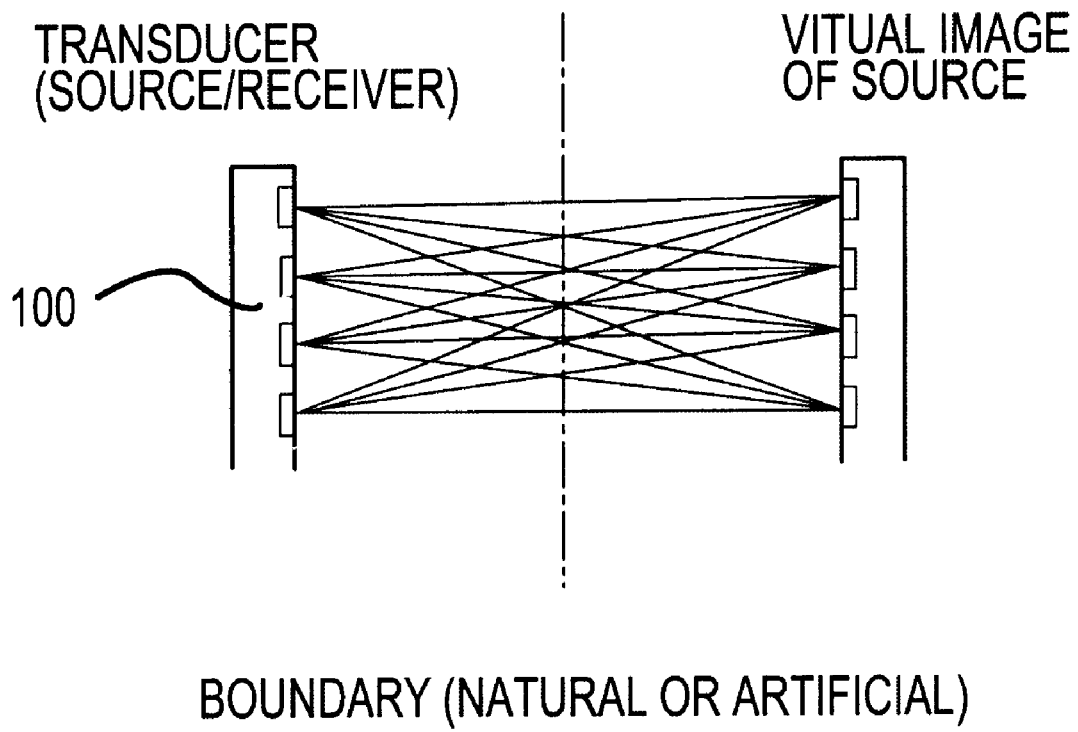
FIG. 7 is a depiction of the intersecting paths of acoustic rays possible from a transducer source.

In accordance with yet another embodiment of the present invention, temperature can be monitored using a tomographic approach (in addition to FIG. 6 embodiment). With reference to FIG. 7 the intersecting path of a transducer 100 having multiple elements is illustrated. The path of propagation is determined by the diffraction of the source and the properties of the medium. Along a path s the acoustic time-of-flight, T will be the integral of the incremental delays over s $$\tau = \int \frac{ds}{v(s)} \tag{3}$$

It should be appreciated that the acoustic propagation will consist of phase retardation (additional delay) and diffraction loss (amplitude loss), refraction, and various tissues with associated speed of sound characteristics, and each of these factors can, if desired, be included in the analysis.

Figure 8:
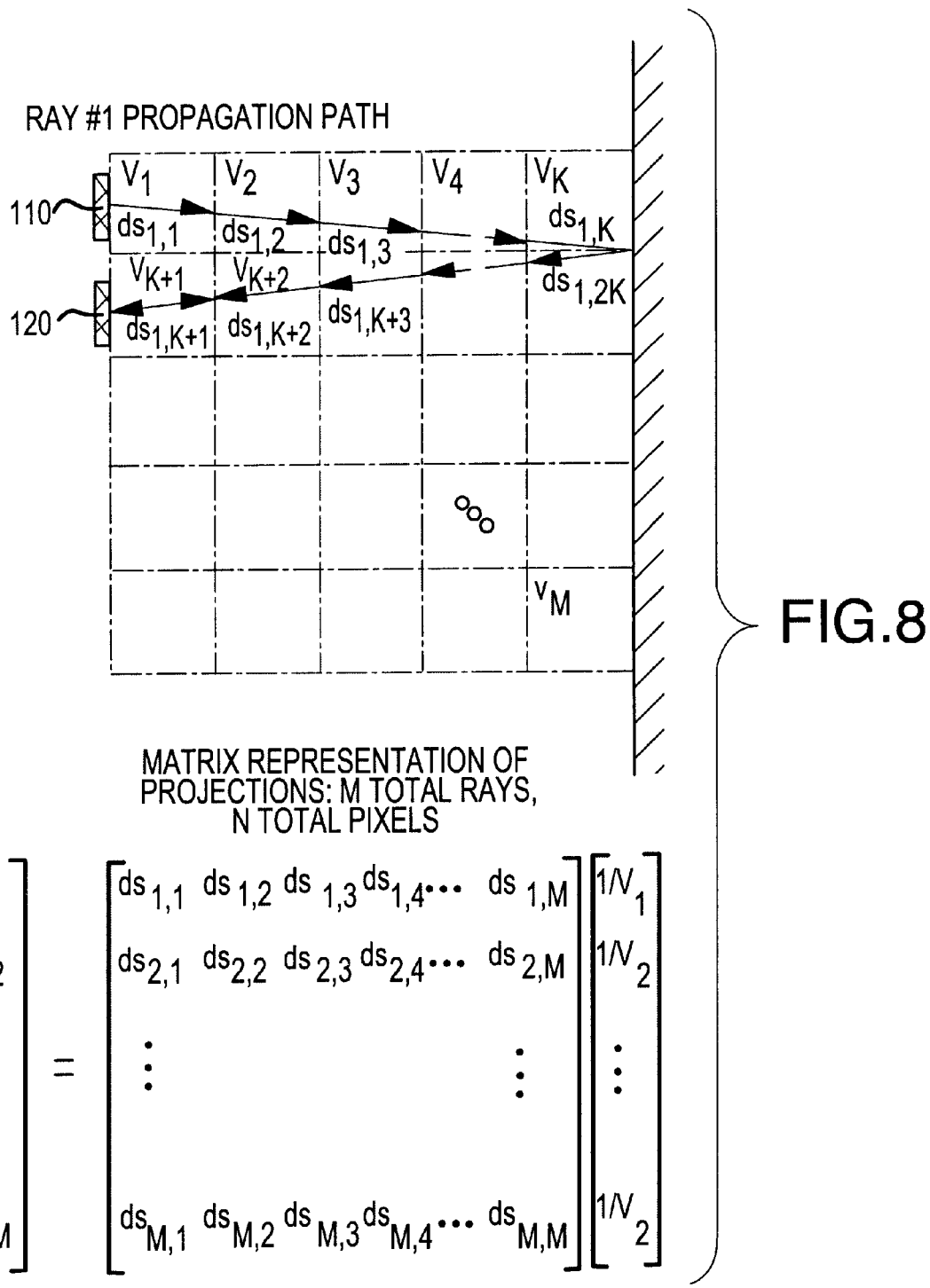
FIG. 8 illustrates a tomographic configuration useful in connection with yet another embodiment of a temperature monitoring subsystem according to the present invention.

In any event, by considering the intersecting paths, such as shown in FIG. 7, superimposed over a grid of pixels, where each pixel represents an area (volume) a tomographic configuration shown in FIG. 8 is obtained. By tracing the propagation and reception of the rays a solution to the velocity in each pixel from the matrix can be calculated according to the following equation:

$$[\tau] = [ds]\left[\frac{1}{v}\right] \tag{4}$$

where $[\tau]$ is a vector of measured delays, $[ds]$ a matrix of known distances and $[\frac{1}{v}]$ a vector of slowness, the reciprocal of the speed of sound (and thus temperature) in each pixel. Given the dependence of the speed of sound in tissue with temperature, the spatial temperature distribution in each pixel is thus determined. As noted briefly above, other factors including acoustic diffraction (beam spreading) and the temperature coefficients of tissue can be incorporated to enhance the accuracy of this method. In accordance with a particularly preferred aspect, as will be described in more detail below, the array can be rotated to allow for a three-dimensional imaging as well as a map of temperature to be measured.

By measuring the ray paths and then heating the region and rapidly re-measuring an accurate spatial map of heating is obtainable, such map being substantially free of tissue motion artifacts.

As described above, the ultrasonic therapy system of the present invention includes an acoustic transducer assembly (in other words, the acoustic transducer subsystem), a therapy subsystem (in other words, a therapeutic heating subsystem), and a temperature monitoring subsystem as well as an appropriate display and control interface. This architecture non-invasively provides essential functions of real-time imaging and temperature monitoring of the treatment region during the therapeutic treatment process. This enables the user to obtain the feedback of the results of the therapeutic treatment process, resulting in improved control of the process. By using the disclosed system of the present invention, safe, automated, and well-controlled procedures for the therapeutic treatment process are achieved at low cost and in only seconds or minutes of therapy. The use of the disclosed transducer capable of imaging, therapy, and monitoring allows precise geometric placement and monitoring of lesions, which has not previously been possible with prior art systems and/or methodologies.

With reference to FIGS. 9A–D and 10A–B, the performance of a transducer made in accordance with the present invention will now be described. Specifically, a 5×5 mm therapy transducer has been constructed in accordance with the present invention and the characteristics of that transducer determined.

Figure 9B:
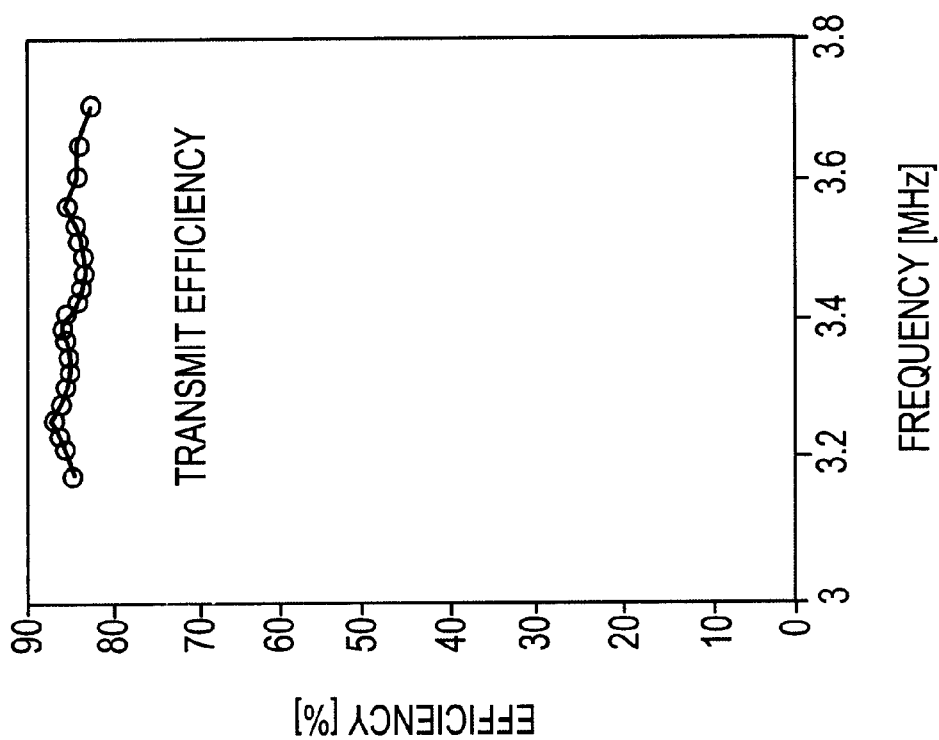
Figure 9A:
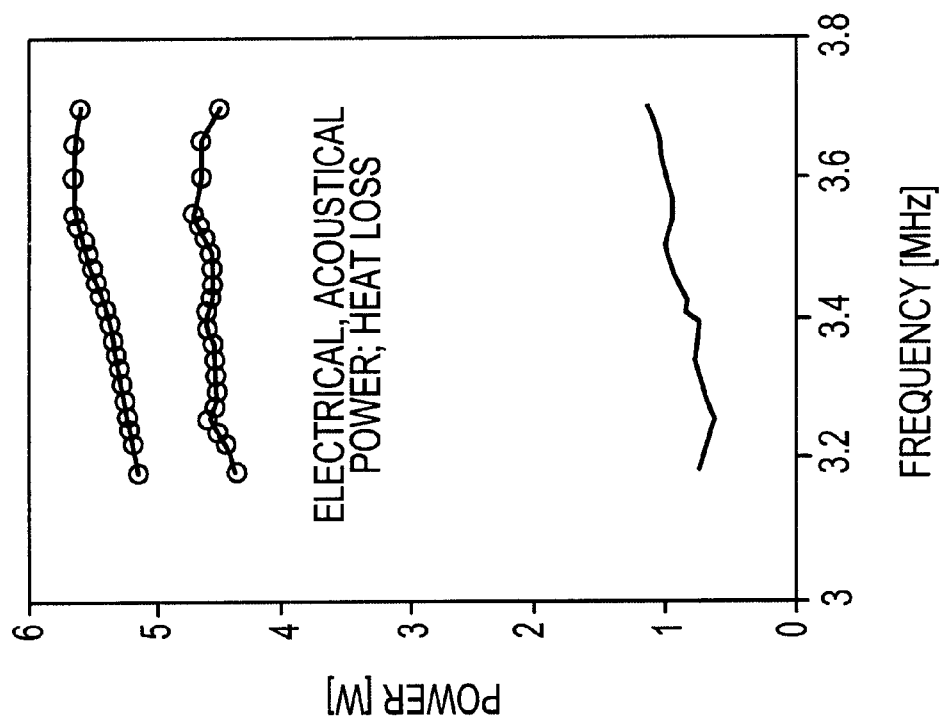

With respect to FIG. 9A, for example, the power versus frequency plot shown therein shows the electrical input, acoustical output and heat loss curves, respectively. As will be appreciated, each of these aspects are well within desirable ranges. Similarly, and with reference now to FIG. 9B, the transmit efficiency of the transducer over the range of 3–4 MHZ is on the order of above 80%, which, as will be appreciated by those skilled in the art, is more than acceptable. It should be appreciated that any suitable frequency range could be utilized.

Figure 9D:
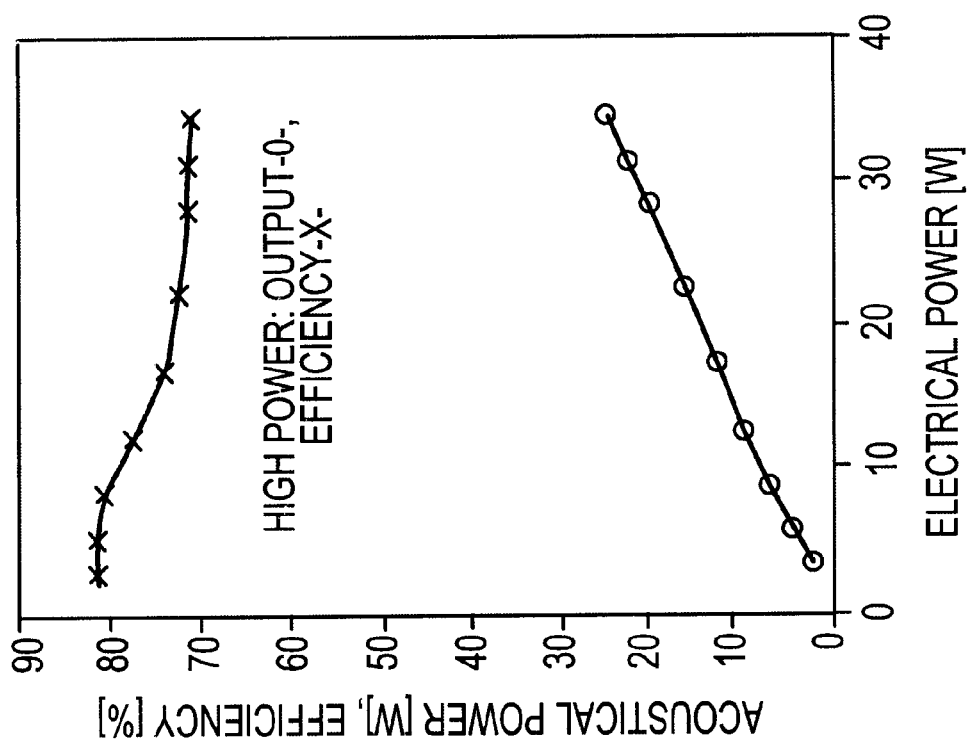
Figure 9C:
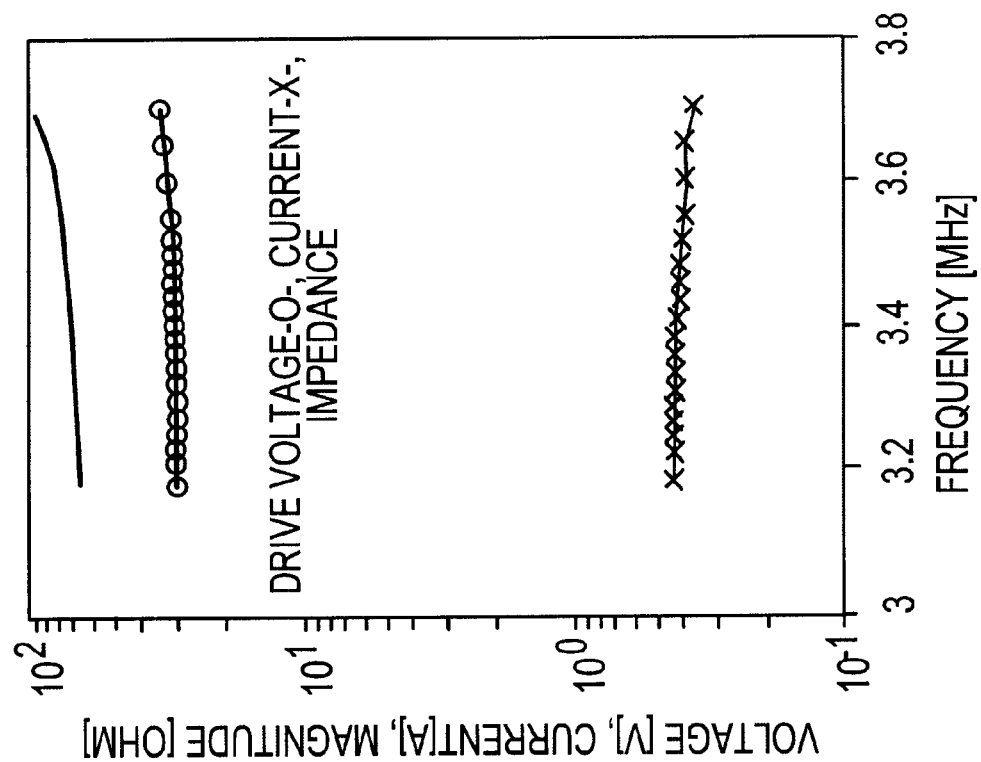

Referring now to FIG. 9C, the voltage, current and impedance magnitude of the transducer over a similar frequency range (e.g., 3–4 MHZ) is shown. In accordance with this particular embodiment, the drive voltage is on the order of about 30 volts, the current on the order of about 400 milliamps, and the impedance magnitude on the order of about 70 ohms.

Finally, with respect to FIG. 9D, the acoustical power at high power outputs is shown, and, as such, it can be seen that as electrical power is increased, the heating efficiency drops. However, over acceptable ranges, transducers made in accordance with the present invention exhibit acceptable performance.

Referring now to FIG. 10, the pulse echo waveform of the aforementioned exemplary transducer is shown in FIG. 10A and the frequency spectrum of the echo, without electrical tuning, is shown in FIG. 10B. As will be appreciated by those skilled in the art, the frequency spectrum and echo voltage plots evidence the usability and functioning of transducers made in accordance with the present invention. Specifically, it will be noted that the transducers exhibit high fractional bandwidth. Although the specific transducer used in gathering the data shown in FIG. 10 comprises a transducer with a single matching layer and no electrical tuning, providing two or more matching layers, as noted above, and electrically tuning the transducer may enhance such characteristics to over 50% or more.

As discussed above, a need exists for therapeutic ultrasonic systems to further provide enhanced imaging and treatment capabilities, such as three-dimensional imaging and temperature information, and three-dimensional therapeutic heating. In that regard, a combined imaging, therapy and temperature monitoring system comprising a single acoustic transducer 100 can be configured to provide a three-dimensional system and thus facilitate enhanced imaging and treatment capabilities. In accordance with this aspect, the three-dimensional system can provide volumetric information relating to the target tissue 800. By facilitating three-dimensional imaging and temperature monitoring of the target tissue 800, the three-dimensional system enables medical practitioners to more readily ascertain the location, as well as the depth, of the treatment region. Accordingly, with the enhanced imaging and temperature monitoring of the treated region, therapeutic heating can be concentrated within a more specific area of the target tissue 800, thus resulting in improved therapeutic results.

Continuing in accordance with this aspect of the invention, the three-dimensional imaging, therapy and temperature monitoring system can be configured in various manners depending upon the particular application as well as various cost considerations. For example, the three-dimensional system can comprise a single acoustic transducer 100 configured to provide only three-dimensional imaging, three-dimensional mapping of temperature, or three-dimensional therapeutic heating of the treatment region. Further, the three-dimensional system can be suitably configured to provide both three-dimensional imaging and three-dimensional temperature mapping, or may include either feature with three-dimensional therapeutic heating. In accordance with a preferred aspect of the invention, the single acoustic transducer 100 is configured to provide all three features, i.e., three-dimensional imaging, therapy and temperature monitoring.

In accordance with another aspect of the invention, the single transducer 100 can be suitably diced to form a 1-dimensional array, such as is described above. Additionally, the single transducer 100 can be suitably diced in two-dimensions to form a two-dimensional array. For example, with reference to FIG. 14, an exemplary two-dimensional array 1400 can be suitably diced into two-dimensional portions 1402. The two dimensional portions 1402 can be suitably configured to focus on the treatment region at a certain depth, and thus provide respective slices 1404 of the treatment region. As a result, the two-dimensional array 1400 can provide a two-dimensional slicing of the image plane of a treatment region 1406.

To provide three-dimensional imaging, temperature monitoring and therapeutic heating of the target tissue 800, the three-dimensional system can comprise a single acoustic transducer 100 configured with an adaptive algorithm, such as, for example, three-dimensional graphic software, contained in a control subsystem, such as, for example, the imaging subsystem 200, the therapeutic subsystem 300 or the temperature monitoring subsystem 400. The adaptive algorithm is suitably configured to receive two-dimensional imaging and temperature information relating to the region-of-interest, process the received information, and then provide corresponding three-dimensional imaging and temperature information. In accordance with this aspect of the invention, the three-dimensional system suitably comprises a two-dimensional array 1400 to provide two-dimensional information to the control subsystem. Accordingly, the adaptive algorithm may suitably receive slices 1404 from different image planes of the treatment region, process the received information, and then provide volumetric information 1406, e.g., three-dimensional imaging and temperature information. Moreover, after processing the received information with the adaptive algorithm, the two-dimensional array 1400 may suitably provide therapeutic heating to the volumetric region 1406 as desired.

Alternatively, rather than utilizing an adaptive algorithm, such as three-dimensional software, to provide three-dimensional imaging or temperature information, the three-dimensional system can comprise a single transducer 100 configured to operate from various rotational positions relative to the target tissue 800. In accordance with this aspect of the invention, the single transducer 100 may be suitably configured in a one-dimensional array or a two-dimensional array, such as array 1400. For example, with reference to FIG. 11, the single transducer 100 can be configured to rotate around a perimeter 1104 of the treatment region to provide three-dimensional imaging and temperature information. Moreover, the single transducer 100 can be configured to rotate around an axis 1102 to provide three-dimensional information. Still further, the single transducer 100 can be configured to translate or sweep along an axis 1103 to provide a larger field-of-view and thus facilitate additional three-dimensional information. The rotational movement can comprise movement in either a clockwise or counter-clockwise direction, or both. Further, the rotational movement could include complete or partial rotations. Thus, the rotational movement could include movement between only two positions, or between any other number of rotational positions. Accordingly, the three-dimensional system 1100 may comprise a single transducer having any rotational and/or translational arrangement suitably configured to provide three-dimensional information.

Moreover, the movement of the single acoustic transducer 100 in various rotational and/or translational positions can be controlled by any mechanical scanning device now known or hereinafter devised for automated movement. However, the rotational movement of the single acoustic transducer 100 may also be controlled by manually placing the acoustic transducer 100 in various desired rotational positions.

Still further, while the three-dimensional system may include a single acoustic transducer configured with a two-dimensional array 1400 and an adaptive algorithm to provide three-dimensional imaging, temperature monitoring and therapeutic heating to a treatment region 1406, the three-dimensional system may be configured to include both an adaptive algorithm and rotational and/or translational movement to provide additional information. As such, an even larger area of treatment may be obtained through the use of both the adaptive algorithm and the rotational and/or translational movement.

Continuing with this example, the three-dimensional system can be suitably configured to capture imaging and temperature information and provide therapeutic heating from the acoustic transducer 100 once the transducer 100 becomes fixedly maintained at various rotational positions. Further, the three-dimensional system can also be suitably configured to capture imaging and temperature information and provide therapeutic heating just prior to, or just after, becoming fixedly positioned. Moreover, the three-dimensional system can be configured to capture imaging and temperature information and provide therapeutic heating during movement around the various rotational positions.

Having obtained imaging and temperature information corresponding to a three-dimensional representation of the treatment region within the target tissue 800, whether through the use of an adaptive algorithm, such as three-dimensional software, rotational movement of the acoustic transducer, or both, improved therapeutic treatment can be facilitated by the imaging, therapy and temperature monitoring system 1100. Moreover, imaging and temperature information can be accumulated to provide three-dimensional representation of the image and temperature within the treatment region which enables the system 1100 to more readily ascertain the location and depth, as well as temperature of the region-of-interest. Still further, based on the three-dimensional information, the system 1100 can be suitably automated if desired to provide therapeutic treatment to a selected volume within the region-of-interest.

In accordance with another embodiment of an ultrasonic system for providing therapeutic treatment, a single ultrasonic probe may be provided which includes at least two acoustic transducers configured within the probe. In accordance with this exemplary embodiment, at least one of the acoustic transducers is configured to facilitate imaging, temperature monitoring and therapeutic heating for a treatment region. With reference to FIG. 12, an exemplary embodiment of such an ultrasonic system 1200 is shown.

In accordance with this exemplary embodiment, the ultrasonic system 1200 suitably comprises a single probe 1202 having at least two acoustic transducers 1204 and 1206. The single probe 1202 comprises any conventional probe configured for having multiple transducers within. In the exemplary embodiment, the probe 1202 comprises a cylindrical endoscope. However, the probe 1202 may also comprise a catheter or a cystoscope and the like. Additionally, as will be described in more detail below, the single probe 1202 may be rotatably connected to the ultrasonic system 1200 to permit rotational movement of the acoustic transducers 1204 and 1206. Moreover, although only two acoustic transducers 1204 and 1206 are shown, the single probe 1202 may suitably include any number of acoustic transducers.

The acoustic transducers 1204 and 1206 are suitably configured within the probe 1202 to provide imaging, temperature monitoring and therapeutic treatment of the treatment region. Notably, at least one of transducers 1204 and 1206 comprises a single transducer 100 for providing imaging, temperature monitoring and therapeutic heating, i.e., at least one of transducers 1204 and 1206 can facilitate all three functions, imaging, temperature monitoring and therapeutic heating. Moreover, each transducer 1204 and 1206 may separately provide imaging, temperature monitoring and therapeutic heating. In addition, transducers 1204 and 1206 may be configured with various ranges of operating frequency, such as, for example, between 1 to 18 MHZ or more.

In accordance with another aspect of the invention, transducers 1204 and 1206 are suitably configured in different positional orientations within probe 1202. In accordance with the exemplary embodiment, the transducers 1204 and 1206 are suitably configured in substantially opposing directions. Accordingly, transducers 1204 and 1206 can provide respective fields-of-view (image or treatment planes) 1208 and 1210 which represent separate regions-of-interest. Moreover, by rotating probe 1202, for example, such as by rotational movement 1212, each transducer 1204 and 1206 can provide either field-of-view 1208 or 1210, or various fields-of-view in between.

Although the fields-of-view 1208 and 1210 are shown as separate regions-of-interest, the transducers 1204 and 1206 may also be suitably positioned within the probe 1202 such that the fields-of-view 1208 and 1210 suitably overlap. Accordingly, the ultrasonic probe 1202 of the exemplary embodiment can suitably provide simultaneous operation within two regions-of-interest, or can provide sequential operations within the same region-of-interest. Moreover, as a result of the above rotational configurations, three-dimensional imaging and temperature information can also be readily obtained. Still further, by operating transducers 1204 and 1206 simultaneously, the imaging, temperature monitoring, and therapeutic heating can be suitably provided over a larger area of the target tissue if desired.

In accordance with another aspect of this exemplary embodiment, the transducers 1202 and 1204 may be suitably configured with different operating frequencies. Thus, transducer 1202 may be configured for high frequency imaging, for example, between 12 to 18 MHZ, while transducer 1204 may be configured for low frequency imaging, for example, between 3 to 5 MHZ. Moreover, transducer 1202 may be configured for low frequency imaging while transducer 1204 is configured for high frequency imaging. By having such different frequencies, particularly if operating simultaneously, transducers 1202 and 1204 can suitably provide capabilities of both high frequency, which facilitates high resolution imaging, and low frequency, which easily controls beamwidth and depth of penetration. Accordingly, an ultrasonic probe can be realized which provides a wider range of imaging information.

In accordance with another embodiment of an ultrasonic system for providing therapeutic treatment, an extracorporeal probe, for example, one outside the body, having at least one acoustic transducer may be included with an endoscopic or cystoscopic probe and the like, for example, one proximate to the target tissue, also having at least one acoustic transducer. Further, both probes are suitably oriented such that the respective transducers are configured to operate on substantially the same treatment region. As a result, therapeutic heating can be focused towards the treatment region in a manner that provides increased intensity. In accordance with this exemplary embodiment, at least one of the acoustic transducers is configured to facilitate imaging, temperature monitoring and therapeutic heating for a treatment region. With reference to FIG. 13, an exemplary embodiment of such an ultrasonic system 1300 is shown.

In accordance with this exemplary embodiment, the ultrasonic system 1300 suitably comprises a extracorporeal probe 1302 and an endoscopic probe 1304. The extracorporeal probe 1302 suitably comprises any conventional probe configured for external or non-invasive use. Accordingly, the single extracorporeal probe 1302 is suitably configured outside a body region 1312, for example, proximate a bodily surface 1310. Meanwhile, the single endoscopic probe 1304 suitably comprises any conventional probe, such as, for example, endoscopic, cystoscopic, or catheter-based probe and the like, configured for invasive use proximate to a target tissue 800. Accordingly, the single endoscopic probe 1304 is suitably configured within a body region 1312 and proximate the target tissue 800. Moreover, although only a single acoustic transducer 1306 and 1308 are respectively shown for the probes 1302 and 1304, any number of acoustic transducers may be included within the probes 1302 and 1304.

The acoustic transducers 1306 and 1308 are suitably configured within the probes 1302 and 1304, respectively, to provide imaging, temperature monitoring and therapeutic treatment of the treatment region. Notably, at least one of transducers 1306 and 1308 comprises a single transducer 100 for providing imaging, temperature monitoring and therapeutic heating. Moreover, each transducer 1306 and 1308 may separately provide imaging, temperature monitoring and therapeutic heating. In addition, transducers 1306 and 1308 may be configured with various ranges of operating frequency, such as, for example, between 1 to 18 MHz or more. As a result, the ultrasonic system 1300 can obtain multiple amounts of information from probes 1302 and 1304 regarding the imaging and temperature monitoring of a desired treatment region within the target tissue 800, while also providing an increase in the intensity of the therapeutic treatment of the treatment region.

The present invention has been described above with reference to various exemplary embodiments. However, those skilled in the art will recognize that changes and modifications may be made to the exemplary embodiments without departing from the scope of the present invention. For example, the various transducers, probes and other components may be implemented in alternate ways, or may be comprised of different materials and thicknesses, depending upon the particular application or in consideration of any number of performance criteria associated with the operation of the system. Further, the number of transducers and probes configured within the various exemplary embodiments is not limited to those described herein. In addition, the techniques described herein may be extended or modified for use with other modes of ultrasonic therapy in addition to the therapeutic heating system of the exemplary embodiments. These and other changes or modifications are intended to be included within the scope of the present invention, as expressed in the following claims.

We claim:

1. A method for therapeutic treatment comprising the steps of:
   providing an ultrasonic therapy system including a single acoustic transducer, a display, and a control interface; and operating said control interface to control said single transducer to non-invasively provide three-dimensional real-time imaging and temperature monitoring, and provide therapeutic heating of a treatment region during the therapeutic treatment process, such that said three-dimensional real-time imaging, temperature monitoring, and therapeutic heating are conducted through the use of said single transducer.

2. The method of claim 1, wherein said step of operating said control interface to control said single transducer comprises adapting two-dimensional imaging signals and temperature signals from said single transducer to provide a three-dimensional representation of said imaging and temperature signals.

3. The method of claim 2, wherein said step of adapting said two-dimensional imaging signals and temperature signals comprises using an adaptive algorithm for reconfiguring said signals to represent three-dimensional images and temperature monitoring.

4. The method of claim 3, wherein said step of adapting said two-dimensional imaging signals and temperature signals comprises using a two-dimensional transducer array.

5. The method of claim 2, wherein said step of operating said control interface to control said single transducer further comprises repositioning said single transducer around a perimeter of said treatment region to provide a three-dimensional representation of said imaging and temperature signals.

6. The method of claim 1, wherein said step of operating said control interface to control said single transducer comprises repositioning said single transducer around a perimeter of said treatment region.

7. The method of claim 6, wherein said step of repositioning comprises using a mechanical scanning device to reposition said single transducer.

8. The method of claim 6, wherein said step of repositioning comprises repositioning said single transducer to at least two positions around said perimeter of said treatment region.

9. The method of claim 6, wherein said step of repositioning comprises repositioning said single transducer substantially around said perimeter of said treatment region.

10. The method of claim 8, wherein said step of repositioning comprises repositioning said single transducer in a substantially continuous manner.

11. The method of claim 8, wherein said step of repositioning comprises at least one of rotating and translating said single transducer.

12. The method of claim 1, wherein said step of operating said control interface to control said single transducer comprises providing three-dimensional therapeutic heating of said treatment region.

13. A combined imaging, therapy and temperature monitoring system comprising:

a single acoustic transducer which enables three-dimensional ultrasonic imaging of a target tissue on a display, temperature measurement of said target tissue by creating a map of the temperature distribution in said target tissue on said display, and substantially controlled heating of said target tissue.

14. The system of claim 13, wherein said single transducer further enables a three-dimensional map of said temperature distribution.

15. The system of claim 13, further comprising a control system, wherein said three-dimensional imaging is facilitated by an adaptive algorithm within said control system which is configured to adapt a two-dimensional imaging signal into a three-dimensional representation of said target tissue.

16. The system of claim 15, wherein said single transducer is configured in a two-dimensional array.

17. The system of claim 13, wherein said three-dimensional imaging is facilitated by repositioning said transducer around a perimeter of said target tissue.

18. The system of claim 17, wherein said repositioning of said transducer around a perimeter of said target tissue is conducted by a mechanical repositioning device.

19. The system of claim 17, wherein said repositioning of said transducer around a perimeter of said target tissue is conducted between at least two positions.

20. The system of claim 17, wherein said repositioning of said transducer around a perimeter of said target tissue comprises at least one of rotating and translating said single transducer.

21. The system of claim 15, further comprising repositioning said transducer around a perimeter of said target tissue.

22. An ultrasonic system for providing therapeutic treatment, said system comprising:

at least two acoustic transducers configured within a single probe wherein at least one of said acoustic transducers is provides all of imaging, temperature monitoring and therapeutic heating for a treatment region.

23. The ultrasonic system of claim 22, wherein said at least two acoustic transducers are positioned within said probe in substantially opposite directions.

24. The ultrasonic system of claim 23, wherein said single probe is rotated around a perimeter of said treatment region to provide an alternate plane-of-view for each said acoustic transducer.

25. The ultrasonic system of claim 22, wherein said at least two acoustic transducers operate at different operating frequencies.

26. The ultrasonic system of claim 22, wherein said system comprises:

at least three acoustic transducers configured within a single probe, wherein at least two of said acoustic transducers are adapted to separately provide imaging, temperature monitoring and therapeutic heating for a treatment region.

27. An ultrasonic system for therapeutic treatment, said system comprising:

a first transducer within an extracorporeal probe;

a second transducer within an endoscopic probe;

wherein at least one of said first transducer and said second transducer provides all of imaging, temperature monitoring and therapeutic heating for a treatment region.

28. The ultrasonic system of claim 27, further comprising additional transducers configured to provide imaging, temperature monitoring and therapeutic heating for treatment region.

* * * * *